United States Patent [19]
Fremeau, Jr. et al.

[11] Patent Number: 5,580,775
[45] Date of Patent: Dec. 3, 1996

[54] HIGH AFFINITY, BRAIN-SPECIFIC NUCLEIC ACIDS ENCODING A L-PROLINE TRANSPORTER, AND VECTORS, AND HOST CELLS COMPRISING THE SAME

[75] Inventors: Robert T. Fremeau, Jr.; Marc G. Caron, both of Durham, N.C.; Randy D. Blakely, Stone Mountain, Ga.

[73] Assignee: Emory University, Atlanta, Ga.

[21] Appl. No.: 879,617

[22] Filed: May 1, 1992

[51] Int. Cl.$^6$ .............................. C12N 15/12; C12N 5/10; C12N 1/19; C12N 1/21

[52] U.S. Cl. .................. 435/240.2; 435/69.1; 435/320.1; 435/254.11; 435/252.3; 536/23.5; 536/24.31

[58] Field of Search ................................ 536/23.5, 24.31; 435/69.1, 320.1, 240.2, 254.11, 252.3

[56] References Cited

PUBLICATIONS

Liu, D. R., et al. (1992) Proc Natl. Acad. Sci. USA 89:6639–43, "A Family of Genes Encoding Neurotransmitter Transporters".

Uhl, G. R. et al. (1992) Mol. Brain Res. 16: 253–59, "Neurotransmitter Transporter Family cDNAs in a Rat Midbrain Library: 'Orphan Transporters' Suggest Sizable Structural Variations".

Askew et al "Molecular Recognition with Convergant Functional Groups, Synthetic and Structural Studies with a Model Receptor for Nucleic Acid Components", *J. Am. Chem. Soc.* 111, 1082–1090.

Balcar et al., "Transport of L–Proline by Rat Brain Slices", *Brain Res.* 102, 143–151 (1976).

Bennett et al., "Amino Acid Neurotransmitter Candidates: Sodium–Dependent High–Affinity Uptake by Unique Synaptosomal Fractions", *Science* 178, No. 4056, pp. 997–999 (1972).

Blakely, et al., "Cloning and Expression of a Functional Serotonin Transporter from Rat Brain", *Nature* 354, 66–70 (1991).

Blakely, et al., "Distinct, Developmentally Regulated Brain mRNAs Direct the Synthesis of Neurotransmitter Transporters", *Journal of Neurochemistry*, vol. 56, No. 1, pp. 860–871 (Jan. 1991).

Capecchi, "The New Mouse Genetics: Altering the Genome by Gene Targeting", *Trends in Genetics*, vol. 5 pp. 70–76 (1989).

Capecchi, "A Strategy for Generating Mice of Any Desired Genotype Through Gene Targeting", *Cell Biology*, Thursday, 2 Feb.: Afternoon Symposia (26–32), No. 3729.

Davis, et al., *Advanced Bacterial Genetics* (Cold Spring Harbor Laboratory, Cold Spring Harbor, N.Y.) (1980). Table of Contents Only.

Fremeau and Popko, "In Situ Analysis of Myelin Basic Protein Gene Expression in Myelin–Deficient Oligodendrocytes: Antisense hnRNA and Readthrough Transcription", *The EMBO Journal*, vol. 9, No. 11, pp. 3533–3538 (1990).

(List continued on next page.)

Primary Examiner—Garnette D. Draper
Assistant Examiner—David L. Fitzgerald
Attorney, Agent, or Firm—Kilpatrick & Cody

[57] ABSTRACT

The anatomical distribution, nucleic acid sequence, pharmacological properties, and inferred structural features of a cDNA encoding a high affinity, $Na^+$-dependent rat brain L-proline transporter is described. The expression of this carrier in subpopulations of putative glutamatergic pathways supports a specific role for L-proline in excitatory amino acid neurotransmission. The cloned transporter cDNA predicts a 637 amino acid protein with 12 putative transmembrane domains and exhibits 44%–45% amino acid sequence identity with other neurotransmitter transporters. These findings support a synaptic role for L-proline in specific excitatory pathways in the CNS. The sequence can be used for expression of the transporter molecule, to make probes for the same protein from other species and related proteins, in diagnostic assays, and to design functional and structural analogs for use in research and possible clinical treatments. The protein is useful in making antibodies, conducting research studies, and design of therapeutic transporter modulators for clinical treatments.

8 Claims, 6 Drawing Sheets

OTHER PUBLICATIONS

Fuerst, et al., "Eukaryotic Transient–Expression System Based on Recombinant Vaccinia Virus that Synthesizes Bacteriophage T7 RNA Polymerase", *Proc. Natl. Acad. Sci. USA* 83, 8122–8126 (1986).

Giros, et al., "Cloning and Functional Characterization of a Cocaine–Sensitive Dopamine Transporter", *FEBS Lett.* 295, 149–154 (1991).

Graham and VanDer, "A New Technique for the Assay of Infectivity of Human Adenovirus 5 DNA", *Virology* 52, 456 (1973).

Hammer, et al., "Spontaneous Inflammatory Disease in Transgenic Rats Expressing HLA–B27 and Human $\beta_2$ m: An Animal Model of HLA–B27–Associated Human Disorders", *Cell* 63:1099–112 (1990).

Hammerman and Sacktor, "Transport of Amino Acids in Renal Brush Border Membrane Vesicles", *J. Bio. Chem.* 252, 591–595 (1977).

Hauptmann, et al., "High Affinity Proline Uptake in Rat Brain Synaptosomes", *FEBS* 0815, vol. 161, No. 2 (Sep. 1983).

Hoffman, et al., "Cloning of a Serotonin Transporter Affected by Antidepressants", *Science* 254, 579–580 (1991).

Hogan, et al., Manipulating the Mouse Embryo, Cold Spring Harbor Laboratory, Cold Spring Harbor, New York (1986) Table of Contents only.

Hollman, et al., "Cloning by Functional Expression of a Member of the Glutamate Receptor Family", *Nature* 342, 643–645 (1989).

Hwang, et al., "Uptake of L–[$^{14}$C]Proline by Isolated Rat Brain Capillaries", *J. Neurochem.* 40, 317–323 (1983).

Joyner, et al., "Production of Mutation in Mouse En–2 Gene by Homologous Recombination in Embryonic Stem Cells", *Nature* 338, 153–156 (1989).

Kanner and Sharon, "Active Transport of L–Proline by Membrane Vesicles Isolated from Rat Brain", *Biochim. Biophys. Acta* 600, 185–194 (1980).

Kennelly and Krebs, "Consensus Sequences as Substrate Specificity Determinants for Protein Kinases and Protein Phosphatases", *J. Biol. Chem.* 266, 15555–15558 (1991).

Kimura, et al., "Isolation and Characterization of Temperature–Sensitive Mutants of Simian Virus 40", *Virology* 49, 394 (1972).

Kozak, M., "An Analysis of 5 '–noncoding Sequences from 699 Vertebrate Messenger RNAs", *Nucleic Acids Research*, vol. 15, No. 20 (Oct. 26, 1987).

Kuhar and Murrin, "Sodium–Dependent, High Affinity Choline Uptake", *J. Neurochem.* 30, 15–21 (1978).

Kyte and Doolittle, "A Simple Method for Displaying the Hydropathic Character of a Protein", *J. Mol. Biol.* 157, 105–132 (1982).

Landschulz, et al., "The Leucine Zipper: A Hypothetical Structure Common to a New Class of DNA Binding Proteins", *Science* 240, 1759–1764 (1988).

Lewis and Dean, "Automated Site–Directed Drug Design: The Formation of Molecular Templates in Primary Structure Generation", *Proc. R. Soc. Lond.* 236, 125–140 and 141–162 (1989).

Lovell–Badge, Teratocarcinomas and Embryonic Stem Cells, A Practical Approach, E. J. Robertson, editor (IRL Press 1987). Table of Contents Only.

McKinlay and Rossmann, "Rational Design of Antiviral Agents", *Ann. Rev. Pharmacol. Toxicol.* 29, 111–122 (1989).

Mei, et al., "A Computational Approach to Mechanism of Self–Cleavage pf Hammerhead RNA", *Proc. Natl. Acad. Sci.* 86:9727 (1989).

Messing, et al., "A System for Shotgun DNA Sequencing", *Nucleic Acids Res.* Vol. 9, No. 2, pp. 309–321 (1981).

Mircheff, et al., "Delineation of Sodium–Stimulated Amino Acid Transport Pathways in Rabbit Kidney Brush Border Vesicles", *J. Membr. Biol.* 64, 113–122 (1982).

Nadler, "Aspartate and Glutamate as Possible Transmitters of Excitatory Hippocampal Afferents", *Nature* 260, 538–540 (1987).

Nadler, "Sodium–Dependent Proline Uptake in the Rat Hippocampal Formation: Association with Ipsilateral–Commissural Projections of CA3 Pyramidal Cells", *J. Neurochem.* vol. 49, No. 4, pp. 1155–1160 (1987).

Nickolson, "'On' and 'Off' Responses of K+–Induced Synaptosomal Proline Release: Involvement of the Sodium Pump", *J. Neurochem.* 38, 289–292 (1982).

Pacholczyk, et al., "Expression Cloning of a Cocaine–and Anti depressant–Sensitive Human Noradrenaline Transporter", *Nature* 350, 350–354 (1991).

Perry and Davies, "The Use of 3D Modelling Databases for Identifying Structure Activity Relationship", *QSAR: Quantitative Structure–Activity Relationships in Drug Design*, pp. 189–193 (Alan R. Liss, Inc. 1989).

Peterson and Raghupathy, "Characteristics of Amino Acid Accumulation by Synaposomal Particles Isolated from Rat Brain", *J. Neurochem.* 19, 1423–1438 (1972).

Potter, "Enhancer–Dependent Expression of Human K Immunoglobulin Genes Introduced into Mouse Pre–B Lymphocytes by Electroporation", *Proc. Natl. Acad. Sci. USA* 81,7161 (1984).

Rebek, "Model Studies in Molecular Recognition", *Science* 235, 1478–1481 (1987).

Rebek, et al., "Convergent Functional Groups 3. A Molecular Cleft Recognizes Substrates of Complementary Size, Shape, and Functionality", *J. Am. Chem. Soc.*, 109, 2426–2431 (1987).

Ripka, "Computers Picture the Perfect Drug", *New Scientist*, 54 –57 (Jun. 16, 1988).

Sandri–Goddin, et al., "High–Frequency Transfer of Cloned Herpes Simplex Virus Type 1 Sequencing to Mammalian Cells by Protoplast Fusion", *Molec. Cell Biol.*, 1, 743 (1981).

Sanger, et al., "DNA Sequencing with Chain–Terminating Inhibitors", *Proc. Natl. Acad. Sci. USA*, 74, 5463–5467 (1977).

Schousboe, A., "Transport and Metabolism of Glutamate and Gaba in Neurons and Glial Cells", *Int. Rev. Neurobiol.* 22, 1045 (1981).

Schwartz, E. A., "Depolarization Without Calcium Can Release $\gamma$–Aminobutyric Acid from a Rentinal Neuron", *Science* 238, 350–355 (1987).

Shimada, et al., "Cloning and Expression of a Cocaine–Sensitive Dopamine Transporter Complementary DNA", *Science*, vol. 254, pp. 576–578 (1991).

Snyder, S. H., "Putative Neurotransmitters in the Brain: Selective Neuronal Uptake, Subcellular Localization, and Interactions with Centrally Acting Drugs", *Biol. Psychiatry* 2, 367–389 (1970).

Snyder, S. H., "Vehicles of Inactivation", *Nature* 354, 187 (1991).

Sompayrac, et al., "Efficient Infection of Monkey Cells with DNA of Simian Virus 40", *Proc. Natl. Acad. Sci. USA* 78, 7575–7578 (1981).

Southern and Berg, "Transformation of Mammalian Cells to Antibiotic Resistance with a Bacterial Gene Under Control of the SV40 Early Region Promoter", *J. Mol. Appl. Gen.* 1:327–341 (1982).

Stevens, et al., "Amino Acid and Sugar Transport", *Ann. Rev. Physiol.* 46, 417–433 (1984).

Tiedge, "The Use of UV Light as a Cross–Linking Agent for Cells and Tissue Sections in In Situ Hybridization", *DNA And Cell Biology*, vol. 10, No. 2 (Mar. 1991).

Wright and Peerce, "Identification and Conformational Changes of the Intestinal Proline Carrier", *J. Biol. Chem.* 259, 14993–14996 (1984).

Zimmer and Gruss, "Production of Chimaeric Mice Containing Embryonic Stem (ES) Cells Carrying a Homoeobox Hox 1.1 Allele Mutated by Homologous Recombination", *Nature* 338, 150–153 (1989).

McCormack, et al., "Leucine–Zipper Motif Update", *Nature* 340, 103–104 (1989).

Sambrook, Frisch & Maniatis, *Molecular cloning: A Laboratory Manual*, 2nd Ed. (Cold Spring Harbor Laboratory, NY 1989). Table of Contents, vol. 1 Only.

```
         |--------------------8--------------------|                                        |---------9--------|
rPROT  SVLGYMSQELGVPVDQVAKA.GPGLAFVIYPQAMTMLPLSPFWSFLTTFMLLTLGLDSQFAFLETIVIAVTDEFPYYLRPKKAVPSGLICVAMY.LMGLI  rPROT
rGAT1  SIVGFMAHVTKRSIADVAAS.GPGLAFLAYPEAVTQLPISPLWAILTTSMLLMLGIDSQFCTVEGFITALVDEYPRLLRNRRELFIAAVCIVSY.LIGLS  rGAT1
hNET   SILGYMAHEHKVNIEDVATE.GAGLVFILYPEAISTLSGSTFWAVFFVMLLALGLDSSMGGMEAVITGLADDFQVLKRHRK.LFTFGVTFSTF.LLALF  hNET
rSERT  TVLGYMAEMRNEDVSEVAKDAGPSLLFITYAEAIANMPASTFAIIFFLMLITLGLDSTFAGLEGVITAVLDEFP.HIWAKREWFVLIVVITCVLGSLL  rSERT
rDAT   SFLGYMAQKHNVPIRDVATD.GPGLIFIIYPEAIATLPLSSAWAAVFFLMLLTLGIDSAMGGMESVITGLVDEFQ.LLHRHRELFTLGIVLATF.LLSLF  rDAT
                                                                                            |----11----|
rPROT  LTTDGGMYWLVLLDDYSAS.FGLMVVITTCLAVTRVYGIQRFCRDIHMMLGFKPGLYF.RACWLFLSPATLLALLVYSIVKYQPSEYGS.YRFPAWAEL  rPROT
rGAT1  NITQGGIYVFKLFDYYSASGMSLLFLVFFECVSISWFYGVNRFYDNIQEMVGSRPCIW.WKLCWSFFTPIIVAGVFLFSAVQMTPLTMGS.YVFPKWGQG  rGAT1
hNET   CITKGGIYVLTLLDTFAAGTSILFA.VLMEAIGVSWFYGVDRFSNDIQQMMGFRPGLY.WRLCWKFVSPAFLLFVVVSIINFKPLTYDD.YIFPPWANW  hNET
rSERT  TLTSGGAVVTLLEEYATGPAVLTV.ALIEAVAVSWFYGITQFCSDVKEMLGFSPGWF.WRICWVAISPLFLLF.IICSFLMSPPQLRLFQYNYPHWSIV  rSERT
rDAT   CVTNGGIYVFTLLDHFAAGTSILFG.VLIEAIGVAWFYGVQQFSDDIKQMTGQRPNLY.WRLCWKLVSPCFLLYVVVSIVTFRPPHYGA.YIFPDWANA  rDAT
               |----12----|
rPROT  LGILMGLLSCLM.IPAGMLVAVLREEGSLWERLQQASRPAIDWGPSLEEN.RTGMYVATLAGSQSPKPLMVHMRKYGGITSFENTAIEVDREIAEEEES  rPROT
rGAT1  VGWLMALSSMVL.IPGYNAYMFLTLKGSLKQPLQVMIQPSEDIVRPENGPE.....QPQAGSSASKEAYI................  rGAT1
hNET   VGWGIALSSMVL.VPIYVIYKFLSTQGSLWERLAYGITPENEHHLVAQRDIRQFQLQHWLAI................  hNET
rSERT  LGYCIGMSS.VICIPTYIIYRLISTPGTLKERIIKSITPETPTEIPCG.DIRMNAV.....  rSERT
rDAT   LGWIIATSSMAM.VPIYATYKFCSLPGSFREKLAYAITPEKDHQLVDRGEVRQFTLRHWLLL................  rDAT
```

HIGH AFFINITY, BRAIN-SPECIFIC NUCLEIC ACIDS ENCODING A L-PROLINE TRANSPORTER, AND VECTORS, AND HOST CELLS COMPRISING THE SAME

The United States government has rights in this invention by virtue of National Institutes of Health grants NS 19576, 2P50-MH 40159, and IP-53-NIH 44211 to M.G.C., and NIDA DA07390-01.

BACKGROUND OF THE INVENTION

Rapid chemical signaling between neurons and target cells is dependent upon the precise control of the magnitude and duration of action of neurotransmitters in synaptic spaces. Two principal mechanisms are responsible for rapid transmitter inactivation. Either the neurotransmitter can be enzymatically metabolized to an inactive product, as with the hydrolysis of acetylcholine by acetylcholinesterase, or the neurotransmitter can be actively transported back into presynaptic nerve terminals or surrounding glial cells by one of a large number of specific, pharmacologically distinguishable membrane transport proteins, as reviewed by Snyder, 1970 *Biol. Psychiatry* 2, 367–389.

Presynaptic nerve endings are enriched for transporters specific to the neurotransmitter they release, thus ensuring constant high levels of neurotransmitters in the nerve terminals, as well as low concentrations in synaptic spaces.

Active transport of neurotransmitters across plasma membranes is energetically coupled to the transmembrane $Na^+$ gradient generated by $(Na^{30}, K^+)$ATPase. Additional ions, including intracellular $K^+$ and extracellular $Cl^-$, are also required for transport of many neurotransmitters. Ion sensitivities of neurotransmitter transporters appear to reflect their cotransport with the neurotransmitter during each translocation cycle. These energetic properties, along with clear pharmacological differences, differentiate the $Na^+$-dependent plasma membrane transporters from the intracellular, $(H^+)$ATPase-coupled vesicular transporters that concentrate neurotransmitters in synaptic vesicles for exocytosis. Although glial cells express $Na^+$-dependent neurotransmitter transporters, as reported by Schousboe, A. (1981) *Int. Rev. Neurobiol.* 22, 1045, the quantitative contribution of glial carriers to synaptic transmission is poorly understood. $Na^+$-dependent transport processes also mediate the presynaptic accumulation of certain substrates for neurotransmitter synthesis. For example, the rate-limiting step in the biosynthesis of acetylcholine appears to be $Na^+$-dependent choline uptake into cholinergic nerve terminals (Kuhar and Murrin, (1978) *J. Neurochem.* 30, 15–21). It has been proposed that during depolarization, physiologically relevant $Ca^{2+}$-independent release of neurotransmitters may occur by reversal of the $Na^+$-dependent uptake process (Schwartz, E. A. (1987) *Science* 238, 350–355).

High affinity, $Na^+$-dependent uptake activities, analogous to the noradrenergic carrier first described at peripheral synapses, have been identified in the mammalian central nervous system (CNS) nerve terminals for the biogenic amine neurotransmitters, including norepinephrine (NE), dopamine (DA), and serotonin (5HT), as reviewed by Snyder, S. H. (1991) *Nature* 354, 187. The association of high affinity, $Na^+$-dependent transport mechanisms in specific neural pathways in the mammalian CNS has provided important information toward the identification of amino acid neurotransmitter candidates. Thus, high affinity, $Na^+$-dependent uptake activities have been identified in synaptosomes and brain slices for the excitatory amino acids L-glutamate and L-aspartate and the inhibitory amino acids gammaaminobutyric acid (GABA) and glycine. Presumably, these uptake activities contribute to the regulation of synaptic levels of the transmitter amino acids.

High affinity, $Na^+$-dependent uptake of L-proline has also been described in rat brain synaptosomes and slices, as reported by Bennett, et al., (1972) *Science* 178, 997–999, Peterson and Raghupathy, (1972) *J. Neurochem.* 19, 1423- 1438, Balcar, et al., (1976) *Brain Res.* 102, 143–151, Hauptman, et al., (1983) *FEBS Lett.* 161, 301–305, and Nadler, (1987) *Nature.* 260, 538–540. Furthermore, like the well-established neurotransmitter amino acids, exogenously loaded radiolabeled L-proline is released from brain slices and synaptosomes in a $Ca^{2+}$-dependent manner following $K^+$-induced depolarization, as reported by Bennett et al., (1974) *Life Sci.* 75, 1045–1056; Balcar et al., (1976) *Brain Res.* 102, 143–151; and Nickolson, (1982) *J. Neurochem.* 38, 289–292.

In contrast, numerous other amino acids that are not thought to have neurotransmitter roles lack high affinity, $Na^+$-dependent synaptosomal uptake activities and are not released to a significant extent from brain slices by $K^+$-induced depolarization (Bennett et al., 1974).

The recent cloning and molecular characterization of specific $Na^+$-dependent membrane transport proteins for GABA and NE established the presence of a distinct gene family of neurotransmitter transport proteins. These transporters possess significant, greater than 46%, but dispersed amino acid sequence identities and exhibit similar inferred topographies. Both transporters are composed of polypeptides of approximately 600 amino acids and contain approximately 12 hydrophobic stretches of 18–25 amino acids that are thought to form transmembrane domains, analogous to findings with other membrane transport proteins. Amino acid sequence conservation among pharmacologically distinct neurotransmitter transporters likely reflects the involvement of these regions in common transport functions, such as the maintenance of transporter topology and/or the coupling of substrate translocation to the transmembrane $Na^+$ gradient. However, no significant sequence similarity is observed with other membrane transport proteins, including the mammalian facilitated glucose carriers, the mammalian $Na^{30}$/glucose cotransporter, the prokaryotic $Na^+$-dependent cotransporters, and the ATP-binding cassette membrane transporters, including the multidrug resistance P glycoproteins and the cystic fibrosis transmembrane conductance regulator.

Recently, cDNA clones have been identified that encode rat brain DA by Giros et al., (1991) *FEBS Lett.* 295, 149–154; Kilty, et al., (1991) *Science* 254, 78–79; and Shimada et al., (1991) *Science* 254, 576–578, and 5HT by Blakely et al., (1991) *Nature* 354, 66–70; Hoffman et al., (1991) *Science* 254, 579–580, transporters. These sequences facilitate further study of the transporters they encode and have potential as diagnostic agents.

It is therefore an object of the present invention to provide a nucleic acid sequence encoding a high affinity, $Na^+$-dependent rat brain L-proline transporter.

It is a further object of the present invention to provide probes for related transporter molecules and for studying function and disorders involving these transporter molecules.

SUMMARY OF THE INVENTION

The anatomical distribution, pharmacological properties, and structural features of a cDNA encoding a high affinity, Na$^+$-dependent rat brain L-proline transporter is described. The expression of this carrier in subpopulations of putative glutamatergic pathways supports a specific role for L-proline in excitatory amino acid neurotransmission.

The polymerase chain reaction (PCR) was used with degenerate oligonucleotides derived from two conserved regions of the norepinephrine and gamma-aminobutyric acid transporters to identify Na$^+$-dependent transporters in rat brain. One PCR product hybridized to a 4.0 kb RNA concentrated in subpopulations of putative glutamatergic neurons including mitral cells of the olfactory bulb, pyramidal cells of layer V of the cerebral cortex, pyramidal cells of the piriform cortex, and pyramidal cells of field CA3 of the hippocampus. Transient expression of the cognate cDNA conferred Na$^+$-dependent L-proline uptake in HeLa cells that was saturable ($K_m$=9.7 μM) and exhibited a pharmacological profile similar to that for high affinity L-proline transport in rat brain slices. The cloned transporter cDNA predicts a 637 amino acid protein with 12 putative transmembrane domains and exhibits 44%–45% amino acid sequence identity with other neurotransmitter transporters. These findings support a synaptic role for L-proline in specific excitatory pathways in the CNS.

The sequence can be used for expression of the transporter molecule in host cells that do not normally express the protein, to make nucleic acid and antibody probes for the same protein from other species and related proteins, in diagnostic assays, and to design functional and structural analogs for use in research and possible clinical treatments. The protein is useful in making antibodies, research studies, and design of modulating compounds for clinical treatments.

BRIEF DESCRIPTION OF THE DRAWINGS

FIG. 1(A) Northern blot analysis. Autoradiograph (1 week) of hybridization of an rTB2-2 cDNA probe to a nylon transfer of total RNAs (20 μg) derived from the indicated rat tissues and rat and human cell lines. A 4.0 kb hybridizing RNA was detected in discrete regions of the rat brain. No specific hybridizing bands were detected in rat adrenal gland or in rat pheochromocytoma (PC12) cells, rat CA-66 medullary thyroid carcinoma cells, human SK-N-SH cells, or human HeLa fibroblasts. Sizes are in kilobases and were determined using RNA standards (Bethesda Research Laboratories).

FIGS. 1B–1E. In situ hybridization. Horizontal FIG. 1B, coronal FIG. 1C, and sagittal FIG. 1D sections of adult rat brain were hybridized with $^{35}$S-labeled antisense RNA derived from PCR fragment rTB2-2. The horizontal section in FIG. 1E was taken adjacent to the section displayed in FIG. 1B but was hybridized with a $^{35}$S-labeled sense-strand control probe. Abbreviations: CA3, pyramidal cell layer of field CA3 of Ammon's horn; CPu, caudate-putamen; Ent, entorhinal cortex; Mi, mitral cell layer of the olfactory bulb; Pir, piriform cortex; Thal, thalamus; V, layer V of the cerebral cortex; VI, layer VI of the cerebral cortex.

FIG. 2 is an alignment of deduced amino acid sequences encoding rat proline, rat GABA, human norepinephrine, rat serotonin, and rat dopamine transporters. Amino acid sequence alignments were produced by iterative use of the BESTFIT routine of the Wisconsin GCG software package. Shaded regions represent sequences absolutely conserved across all five transporters. Solid lines above rPROT reflect location of 12 proposed transmembrane domains. Asterisks denote residues defining the conserved leucine zipper motif. Abbreviations; rPROT, rat proline transporter (SEQ. I.D. No. 9); rGAT1, rat GABA transporter (SEQ. I.D. No. 10); hNET, human norepinephrine (SEQ. I.D. No. 11) transporter; rSERT, rat serotonin transporter (SEQ. I.D. No. 12); rDAT, rat dopamine transporter (SEQ. I.D. No. 13).

FIG. 3A is a graph of the time course of L-[$^3$H] proline accumulation into HeLa cells transfected with pPROT. Na$^+$dependence was examined by isotonic substitution of assay NaCl with choline chloride. Background levels of proline transport were determined by transfecting HeLa cells under identical conditions with pBluescript™ SKII(–). Data represent the mean ± SEM of triplicate determinations. The symbol ■ represents cells transfected with pPROT in the presence of NaCl. The symbol ▲ represents cells transfected with pBluescript™ in the presence of NaCl. The open square symbol represents cells transfected with pPRPT in the presence of choline chloride.

DETAILED DESCRIPTION OF THE INVENTION

Figure 1A:
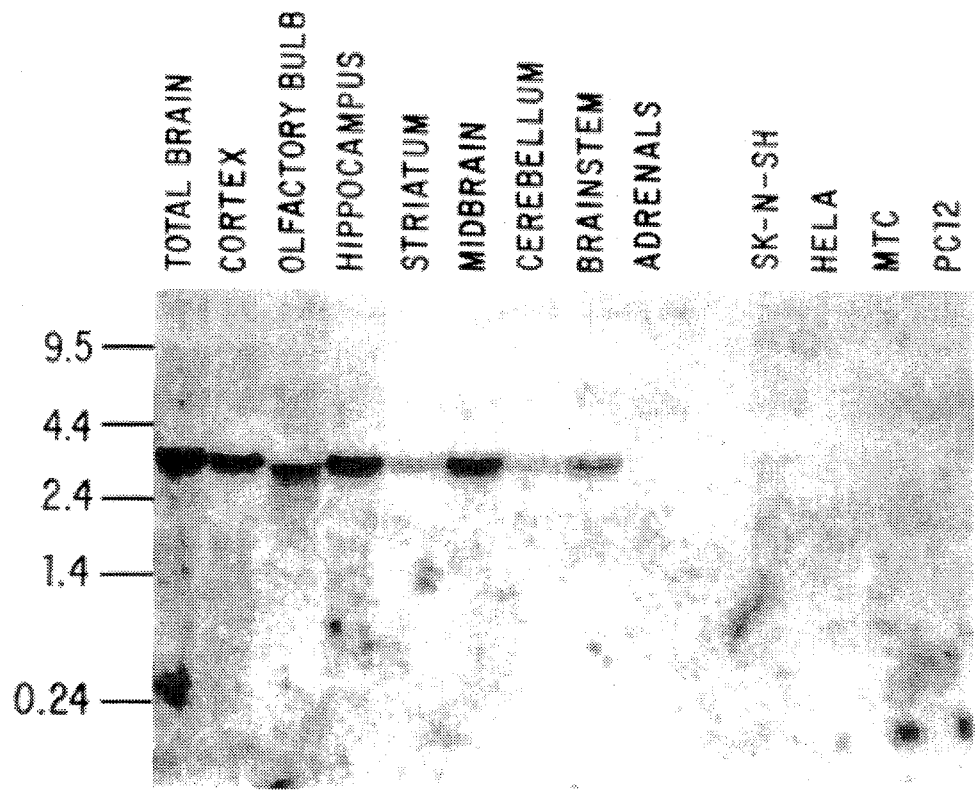
FIGS. 1A–1E Northern Blot and in Situ Localization of RNA Hybridizing to PCR Clone rTB2-2.

The following studies were conducted to determine the anatomical distribution, pharmacological properties, and structural features of a cDNA encoding a high affinity, Na$^+$-dependent rat brain L-proline transporter.
Isolation of Neurotransmitter Transporter Sequences from Rat Brain by PCR Using Degenerate Oligonucleotide Primers To identify previously undetected neurotransmitter transporter proteins expressed in mammalian brain, synthetic degenerate oligonucleotide primers derived from conserved amino acid sequences from the first and sixth transmembrane domains (SEQ. I.D. Nos. 1 and 2, respectively) of the human NE and rat GABA transporters were synthesized and utilized for PCR amplification of rat brain cDNA. Reaction products of approximately 700 bp were purified, subcloned, and sequenced.

Synthetic, degenerate oligonucleotides of sequences shown in the Sequence Listing as SEQ. I.D. Nos. 3 and 4, respectively, (SEQ. I.D. No. 3) (SEQ. I.D. No. 4) were designed to encode two highly conserved amino acid stretches near the first (SEQ. I.D. No. 1) and sixth (SEQ. I.D. No. 2) transmembrane domains, respectively, of the human NE (Pacholczyk et al., 1991) and rat GABA (Guastella et al., 1990) transporters. Residues in SEQ. I.D. No. 3 and residues 1–9 in SEQ. I.D. No. 4 represent addition of 5' restriction sites for cloning. Single-stranded rat brain cDNA was synthesized from poly(A)$^+$ RNA with random hexamer primers as described by the manufacturer (Amersham). Oligonucleotides were combined with single-stranded rat brain cDNA into PCRs conducted with Taq polymerase as described by the manufacturer (Promega) for 30 cycles of 94° C. for 1 minute, 45° C. for 2 minutes, 72° C. for 3 minutes, with a final extension of 15 minutes. Products of approximately 700 bp, after phenol extraction and ethanol precipitation, were digested with EcoRi to prevent recloning the rat GABA transporter (Guastelia et al., 1990), which has an EcoRI restriction site between the oligonucleotides used for amplification, and digested with Xbal and Xhol to produce staggered ends for cloning. Samples were gel purified (Gene Clean, Bio 101), and ligated into Xbal– and Xhol-digested pBluescript™ SKII(–) (Stratagene). Partial sequencing of PCR product rTB2-2 was achieved by dideoxynucleotide chain termination using Sequence (USB).

To isolate a full-length cDNA clone, cDNA from PCR fragment rTB2-2 was used as a template for the synthesis of a 186 bp PCR probe using a 5' sense-strand oligonucleotide of the sequence shown as SEQ. I.D. No. 5 (SEQ. I.D. No. 5) and a 3' antisense oligonucleotide of the sequence shown as SEQ. I.D. No. 6 (SEQ. I.D. No. 6). Oligonucleotides were combined with rTB2-2 template DNA (18 ng) into a PCR in the presence of 400 μCi of [$^{32}$P]dCTP (3000 Ci/mmol) and amplified with Taq polymerase as described by the manufacturer (Perkin Elmer) for 30 cycles of 94° C. for 1 minute, 55° C. for 1 minute, 72° C. for 2 minutes, with a final extension time of 8 minutes. The $^{32}$P-labeled PCR probe was used to screen 1×10$^6$ phage recombinants from a rat forebrain cDNA library in lambda Zap II (Stratagene). Duplicate nylon filters (Biotrans Membranes, Inc.) were hybridized at 42° C. in a buffer containing 5×SSC (1×SSC=0.15M NaCl, 0.015M sodium citrate [pH 7.0]), 5×Denhardt's solution, 0.05M sodium phosphate (pH 6.5), 0.1% SDS, 50% formamide, 200 μg/ml sheared salmon sperm DNA, and 6.2×10$^6$ cpm/ml $^{32}$P-labeled PCR probe. After hybridization, filters were washed for 30 minutes at room temperature (twice) in 1×SSC, 0.1% SDS. The filters were then washed for 15 minutes at 65° C. (twice) in 0.2×, 0.1% SDS. Bluescript plasmids (pB5 SKII(–)) were rescued from plaque-purified positive rTB2-2 cDNA clones by in vivo excision as described by the manufacturer (Stratagene).

The nucleotide sequence was determined on both strands from alkaline lysate minipreps of double-stranded DNA by dideoxynucleotide chain termination using Sequenase. Nucleotide sequences were assembled using Wisconsin GCG programs. Deduced amino acid sequences of rTB2-2-20 were compared with protein sequences translated from nucleotide sequences stored in the GenBank and EMBL data bases. The extent of protein sequence similarity was calculated as described by Dayhoff et al. (1983).

One PCR-derived sequence, rTB2-2, displayed a similar identity in its deduced amino acid sequence (61%–65%) with the previously cloned amino acid (GABA) and biogenic amine (DA, NE, and 5HT) transporters. Because rTB2-2 did not display any greater similarity with the amino acid or the biogenic amine transporters, no initial clues as to the substrate class of this putative transporter could be determined. To gain insights into the possible substrate for this potential transporter, the size and regional distribution of RNA transcripts that hybridize to rTB2-2 in the rodent brain were determined.

rTB2-2 is Encoded by a 4.0 kb mRNA Expressed in Excitatory Pathways in Rat Brain cDNA derived from PCR fragment rTB2-2 (100 ng) was radiolabeled with $^{32}$P-labeled dCTP (50 μCi) using random oligodeoxynucleotide primers (Amersham) and hybridized to a nylon (Zetaprobe, Bio-Rad) transfer of total RNAs (20 μg) derived from rat tissues and rat and human cell lines. The blot was prehybridized at 42° C. in 50% formamide, 5×SSPE (1×SSPE–150 nM NaCl, 10 mM NaH$_2$PO$_4$ [pH 7.4], 1 mM EDTA [pH 8.0]), 5×Denhardt's solution, 10% dextran sulphate, 1% SDS, 100 μg/ml salmon sperm DNA for 2 hours. Probe was added, and hybridization was continued for 14 hours. The blot was rinsed with two 20 minute washes in 2×SSPE, 0.1% SDS (22° C.), followed by a 1 hour rinse at 65° C. in 0.1×SSPE, 0.1% SDS, and then exposed to autoradiographic film with an intensifying screen for 5 days. All lanes were equivalently loaded based on even intensity of ribosomal RNAs. The foregoing conditions are defined herein as standard hybridization conditions.

In situ hybridization was conducted on 4% paraformaldehyde-postfixed adult rat brain sections as previously described (Fremeau and Popko, 1990). Briefly, male Sprague-Dawley rats (300–375 g; Charles River Breeding Laboratories) were killed by decapitation. Brains were removed and frozen on an aluminum block cooled with liquid nitrogen. Frozen sections (10 μm) in the coronal, sagittal, and horizontal planes were prepared in a cryostat, mounted onto room temperature slides (Onasco Biotech, Houston, Tex.) and stored at −70° C. until processed for in situ hybridization. Synthetic [$^{35}$S]UTP-labeled single-stranded RNA was synthesized with the 710 bp PCR fragment rTB2-2, by in vitro transcription from the T3 promoter after plasmid linearization with Xhol (antisense orientation) or from the T7 promoter after linearization with Xbal (sense orientation). Tissue sections were thawed and fixed for 10 minutes in 4% paraformaldehyde in phosphate-buffered saline at 4° C. The sections were rinsed in 2×SSC, covered with a minimal volume of 2×SSC, and illuminated with a germicidal ultraviolet lamp (30 W, wide spectrum ultraviolet light) for 5 minutes at a distance of 30 cm in accordance with the method of Tiedge et al., *DNA Cell Biol.* 10:143–147 (1991). The sections were then rinsed in 2×SSC, covered with prehybridization buffer (50% formamide, 0.6M NaCl, 10 mM Tris-HCl[pH 7.5], 0.02% Ficoll, 0.02% polyvinyl pyrollidone, 0.1% bovine serum albumin, 1 mM EDTA [pH 8.0], 50 μg/ml salmon sperm DNA, 500 μg/ml yeast total RNA, 50 μg/ml yeast tRNA), and stored at 50° C. for 1 hour. Prehybridization buffer was removed, and the slides were covered with hybridization buffer (50% formamide, 0.6M NaCl, 10 mM Tris-HCl (pH 7.5) 0.02% Ficoll, 0.02% polyvinyl pyrollidone, 0.1% bovine serum albumin, 1 mM EDTA [pH 8.0], 10 μg/ml salmon sperm DNA, 50 μg/ml yeast total RNA, 50 μg/ml yeast tRNA, 10 mM dithiothreitol, 10% dextran sulphate) containing $^{35}$S-labeled probes (2.5–5.0×10$^6$ cpm /ml; heat-denatured for 15 minutes at 65° C.). Hybridization was performed for 16–18 hours at 50° C. Following hybridization, the sections were washed for 60 minutes in 2×SSC at 50° C. and then treated with RNAase A (50 μg/ml) for 60 minutes at 37° C. The sections were then washed in 2×SSC for 60 minutes at 50° C., followed by a final high stringency wash in 0.1×SSC, 14 mM β-mercaptoethanol, 0.15% sodium pyrophosphate for 3 hours at 50° C. The heat was turned off, and the slides were allowed to cool gradually to room temperature overnight. The hybridized sections were exposed to XAR autoradiography film (Kodak) for 1 week.

FIG. 1A demonstrates that PCR product rTB2-2 hybridizes to a single 4.0 kb RNA present in multiple regions of rat brain. The strongest hybridization signals are observed in cerebral cortex, hippocampus, and midbrain. Intermediate signals are observed in the olfactory bulb and brain stem, while only weak hybridization is observed in the striatum (caudate-putamen) and cerebellum. No specific hybridizing species were detected in rat adrenal glands or the human SK-N-SH, human HeLa, rat medullary thyroid carcinoma, and rat PC12 cell lines, indicating that PCR fragment rTB2-2 does not represent a ubiquitous transporter that might subserve a general metabolic role.

Figure 1B:
Figure 1C:
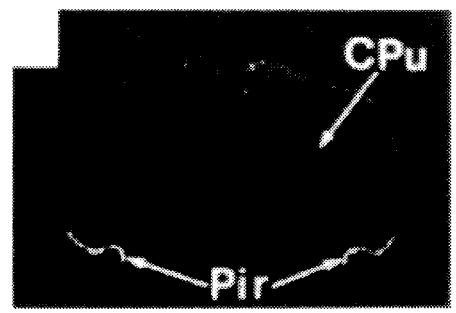
Figure 1D:
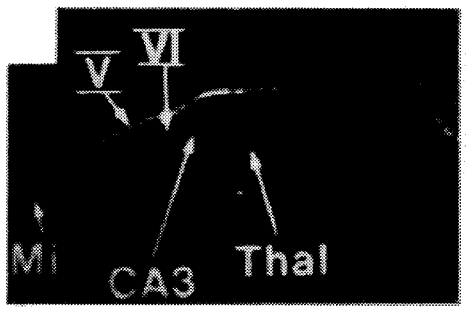
Figure 1E:

To identify more clearly the cellular localization of RNAs hybridizing to PCR product rTB2-2, 4% paraformaldehyde-fixed rat brain sections were hybridized with $^{35}$S-labeled antisense RNA derived from PCR fragment rTB2-2. FIGS. 1B–1D reveal that rTB2-2 mRNA is heterogeneously expressed in adult rat brain. Prominent hybridization signals were observed over subpopulations of putative glutamatergic neurons, including mitral cells of the olfactory bulb, pyramidal cells of layer V of the cerebral cortex, pyramidal cells of the piriform cortex, and the entorhinal cortex. Furthermore, labeled cells were also observed in layer VI of the cerebral cortex, particularly the pericallosal region at all layers examined. Labeled cells were also observed scattered throughout the cerebral cortex. Within the hippocampus, rTB2-2 mRNA was heterogeneously distributed. Prominent hybridization signals were observed over the CA3 pyramidal cells, and moderate labeling was seen over the CA1 pyramidal cells, whereas little or no specific labeling was observed over the granule cells of the dentate gyrus. Moderate hybridization signals were detected over the midbrain, thalamus, hypothalamus, and brain stem. Within the cerebellum, the granule cell layer exhibited specific though less consistent hybridization (FIGS. 1B and 1D). Little or no specific labeling was observed over the caudate-putamen, white matter tracts, choroid plexus, ependymal cells of the cerebral ventricles (FIGS. 1B–1D), or sections hybridized with a sense-strand control probe (FIG. 1E).

Characterization of rTB2-2 cDNAs

PCR fragment rTB2-2 was used to isolate cDNA clones from a rat forebrain cDNA library, described by Hollman, et al., Nature 342, 643–645 (1989). Several candidate clones were obtained, two of which contained the entire coding region of a single 1911 bp open reading frame within which was found the sequence of PCR fragment rTB2-2. The nucleotide and deduced amino acid sequences of clone rTB2-2-20 are shown in the sequence listing as SEQ. I.D. No. 7 and SEQ. I.D. No. 8 respectively.

The first ATG (residues 91–93) present in the cDNA was assigned as the initiation codon on the basis that it conformed to the translation initiation consensus sequence of Kozak Nucl. Acids. Res. 15, 8125–8148 (1987); and because the proposed translation initiation codon is 39 bp downstream from a single in-frame stop codon.

Nucleotide and Deduced Amino Acid Sequences of rTB2-2-20:

Nucleotides are numbered in the 5' to 3' direction beginning with the first residue of the codon for the putative initiator methionine. The stop codon flanking the open reading frame in the amino acid sequence follows met 667 (SEQ. I.D. No. 8). Twelve putative membrane-spanning domains. The precise locations of the borders of the transmembrane domains are arbitrary and are drawn for convenience of representation. One potential N-linked glycosylation site located on the large putative extracellular loop connecting transmembrane domains 3 and 4 occurs at Asn212-Lev213. Two additional putative glycosylation sites are located, one each, within the putative intracellular N- and C-terminal domains. One putative intracellular consensus sequence for cAMP-dependent protein kinase phosphorylation Thr71-Gly72, and three putative intracellular consensus sequences for protein kinase C phosphorylation occur at sThr44-Pro45, SER269-Gly270, and Ser630-Pro631. The remaining two protein kinase A sites and three protein kinase C sites are located in the putative extracellular domains or within the putative transmembrane domains. A polyadenylation signal in the 3' untranslated domain is underlined. A motif resembling a leucine zipper occurs at Lev106-Lev127. PCR fragment rTB2-2 begins at the 5' end with adenine-175 and extends until the 3' end at 884.

The hydropathy plot of the deduced amino acid sequence

Hydropathy was determined by the method of Kyte and Doolittle J. Mol. Biol. 157, 105–132 (1982), with a window size of 19.

The deduced protein sequence (SEQ. I.D. No. 8) predicts a putative protein of 637 amino acid residues with a molecular mass of the primary translation product of 71 kd. Hydropathy analysis of the putative protein reveals the presence of 12 regions of significantly extended hydrophobicity suitable for the formation of transmembrane domains. The N-terminus does not contain a readily identifiable signal sequence, suggesting that the N-terminus resides on the cytoplasmic face of the membrane, as modeled previously for the rat GABA transporter (Guastella et al., 1990). One canonical site for N-linked glycosylation is present on a large hydrophilic domain present between putative transmembrane domains 3 and 4, in a location similar to that observed for a predicted extracellular loop in the other cloned neurotransmitter transporters. One consensus site for cAMP-dependent protein kinase phosphorylation (Kennelly and Krebs, J. Biol. Chem. 266, 13335–15558 (1991)), Thr-14, is present in the N-terminus. Three consensus sites for protein kinase C-dependent protein kinase phosphorylation (Kennelly and Krebs, 1991) are present: one each in the N-terminus (Thr-41) and C-terminus (Ser-600) and one in the putative intracellular loop between transmembrane domains 4 and 5 (Ser-239).

A leucine zipper motif, consisting of 4 leucine residues repeated every seventh amino acid residue, is present in the second putative transmembrane domain. This motif was originally proposed to mediate the dimerization of some DNA-binding protein by Landschutz, et al., (1988) Science 240, 1759–1764; Science 240, 1759–1764. The leucine zipper motif has also been described in membrane proteins including voltage-gated $K^+$ channels (McCormack et al., (1989) Nature 340, 103–104) and glucose transporters (White and Weber, (1989) Nature 340, 103–104), where it may mediate subunit oligomerization in the membrane. This motif is largely conserved across all of the cloned neurotransmitter transporters.

A comparison of the predicted amino acid sequence of rTB2-2-20 with those of cloned neurotransmitter transporters reveals striking amino acid sequence conservation, as demonstrated by FIG. 2. The predicted protein encoded by rTB2-2-20 shows 44%–45% amino acid identity and 65%–68% similarity with the rat GABA (Guastella et al., 1990), human NE (Pacholczyk et al., (1991) Nature 350, 350–354), rat DA (Giros et al., 1991; Kilty et al., 1991; Shimada et al., 1991), and rat 5HT (Blakely et al., 1991a; Hoffman et al., 1991) transporters. Specifically, 148 amino acids are absolutely conserved among the various cloned neurotransmitter transporters. Many of these residues are within or adjacent to the presumed transmembrane domains.

These results indicate that cDNA clone rTB2-2-20 represents a novel member of the emerging family of neurotransmitter transporters.

Expression of rTB2-2-20 in HeLa Cells Confers High Affinity, $Na^+$-Dependent L-Proline Uptake To examine the substrate specificity of the encoded transporter candidate, the 2.2 kb BamHI-XbaI fragment of rTB2-2-20 was subcloned in the sense orientation downstream of the T7 promoter sequence of pCDNA1 (Invitrogen), and the cDNA was transiently expressed in HeLa cells by a T7 vaccinia virus transient expression system (Fuerst et al., (1986) Proc. Natl. Acad. Sci. USA 83, 8122–8126; Blakely et al., 1991b).

A BamH1-XbaI fragment of rTB2-2-20 containing the entire coding sequence was cloned in the sense orientation downstream of the T7 promoter of pcDNA-1 (Invitrogen) (designated pPROT). Hela cells, 100–250,000 per well in 24 well plates, were infected with recombinant vaccinia virus strain VTF7-3 (10 pfu per cell), expressing T7 RNA polymerase (Fuerst et al., 1986), followed 30 min. later by liposome-mediated (3 µg per well; Lipotectin, BRL) transfection of pPROT (1 µg per well). L-Proline transport assays were conducted 8–9 hr. after transfection with L-($^3$H)proline (50 nM, Dupont, New England Nuclear) as substrate in Krebs-Ringer-Tris-HEPES uptake medium as described (Blakely et al., 1991b). Assays were terminated and washed with ice-cold Krebs-Ringer-Tris-HEPES uptake medium, cells were solubilized with 500 µl of 1% SDS, and accumulated radioactivity was determined by scintillation counting. Triplicate control transfections of pBluescript™ SKII(−) done under identical conditions were included on each 24 well plate to determine nonspecific transport values, which were subtracted from signals obtained with pPROT. The Na$^+$dependence of L[$^3$H]proline uptake was determined by isotonic substitution of assay NaCl with choline chloride. To examine the pharmacological specificity of the cloned L-proline transporter, transport assays were conducted for 20 min. with or without the indicated concentrations of selected pharmacological agents added just prior to the addition of L[$^3$H]-proline.

Figure 3A:
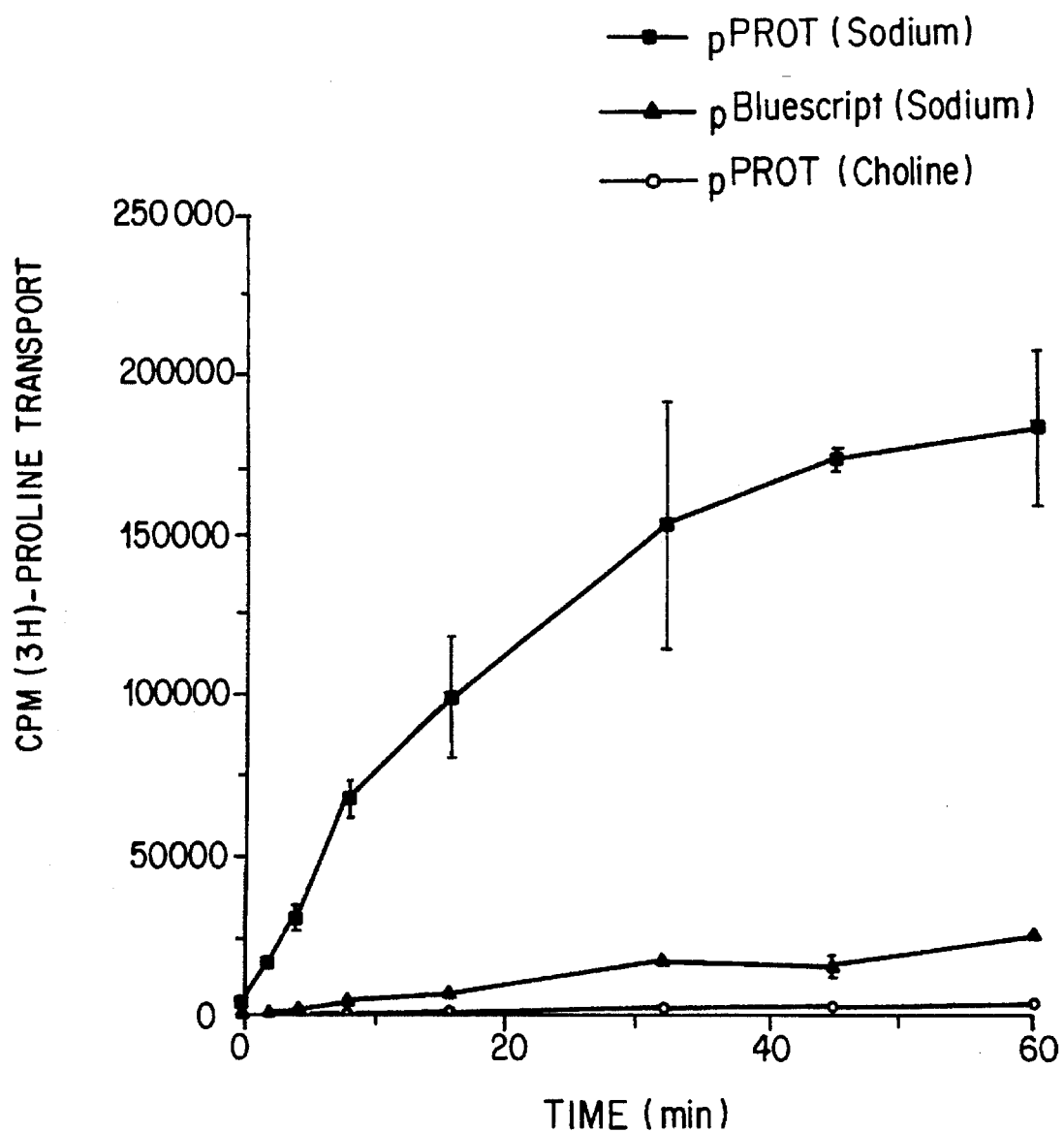
FIGS. 3A and B show the Na$^+$, Time, and Concentration Dependence of L-Proline Uptake in HeLa Cells Transfected with pROT.
Figure 3B:
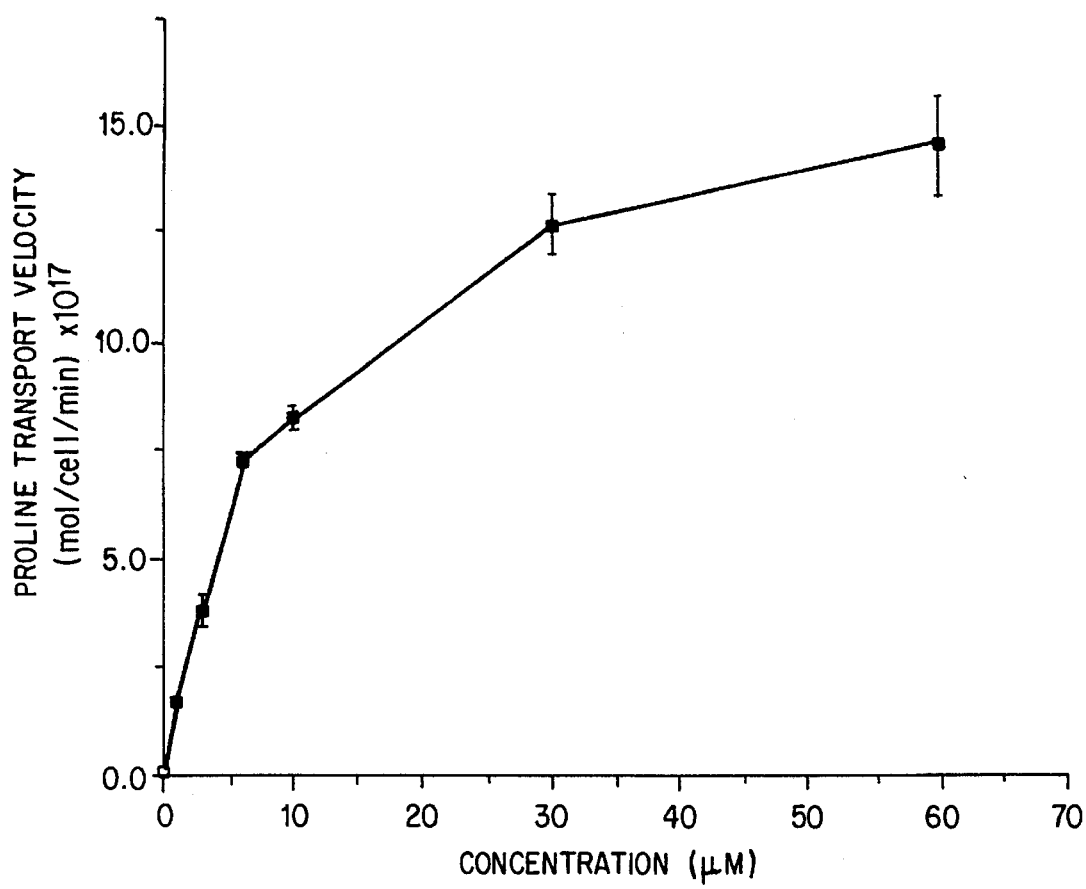
FIG. 3B is a graph of the uptake velocity of 50 nM L-($^3$H)proline determined in the presence of increasing concentrations of unlabeled L-proline during a 20 min. incubation in transfected HeLa cells. Data represent the mean ± SEM of three separate experiments each done in triplicate. Inset: Eadie-Hofstee analysis of initial velocity data.
Figure 3C:
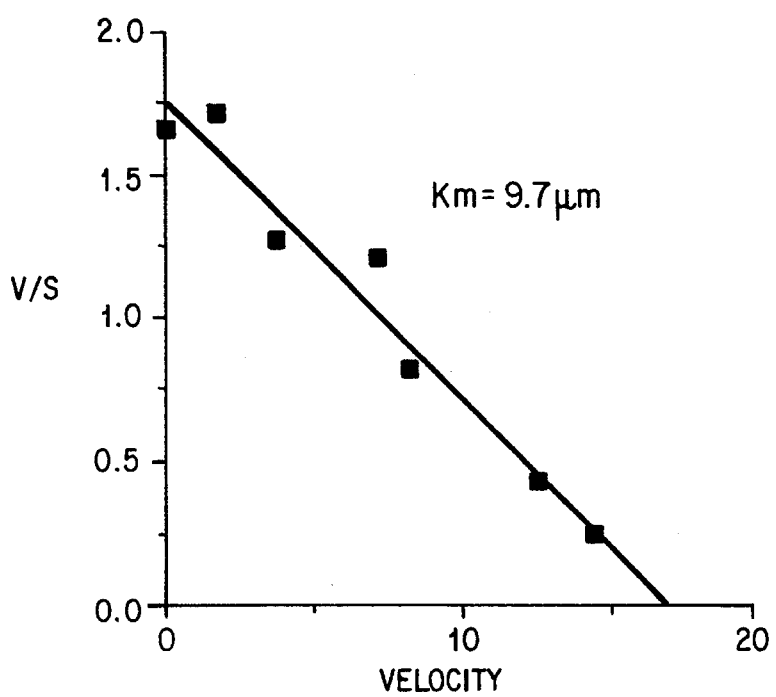

Despite the apparent localization of rTB2-2-20 mRNA in subpopulations of putative glutamatergic cell bodies, transient expression of the novel transporter cDNA did not induce transport of L-[$^3$H]glutamate or D-[$^3$H]aspartate in HeLa fibroblasts, indicating that this clone does not code for an acidic amino acid transporter. However, FIG. 3A demonstrates that HeLa cells transiently transfected with this construct (designated pPROT) express time- and Na$^+$-dependent L-proline uptake. Isotonic substitution of assay NaCl with choline chloride abolished specific L-proline uptake (FIG. 3A). Furthermore, L-proline transport was saturable at low substrate concentrations, exhibiting an apparent Michaelis constant ($K_m$) of 9.7 µM (FIG. 3B).

These results indicate that this cDNA encodes a high affinity Na$^{30}$-dependent rat brain L-proline transporter. Control experiments conducted with plasmid vector-transfected HeLa cells revealed that endogenous L-proline transport, which was less than 10% of pPROT-induced transport, was Na$^+$-dependent (FIG. 3A), and predominantly of low affinity, with a $K_m$ greater than 200 µM.

Pharmacological Specificity of High Affinity L-Proline Transporter

Figure 4:
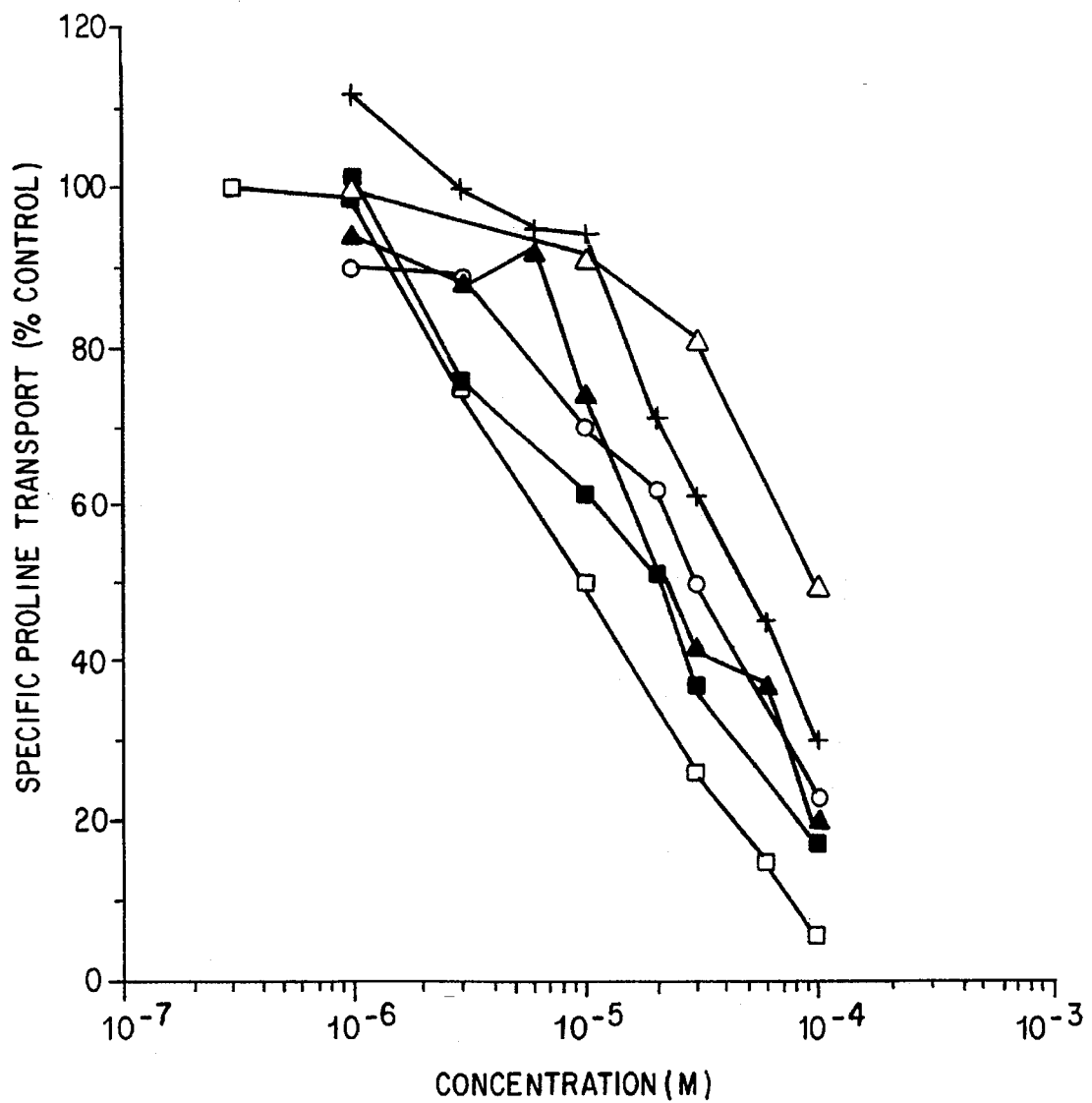
FIG. 4 is a graph of the inhibition of proline transport by structural analogs in transfected HeLa cells. Proline transport assays (50 nM L-([$^3$H]proline) were conducted for 20 minutes with or without increasing concentrations of the indicated pharmacological agents. The pharmacological agents are represented by the following symbols: open square symbol, L-proline; ■, L-pipecolic acid; ▲, sarcosine; open circle symbol, 3,4-dehydroproline; +, L-norleucine; and, open triangle symbol, L-azetidine-2-carboxylic acid. Nonspecific transport, determined by a parallel transfection of pBluescript™ SKII(–), was determined for each assay, and values were subtracted from signals obtained with rPROT. Data represent triplicate determinations of the percentage of specific proline uptake obtained with labeled substrate alone.

L-PROT-induced L-proline transport exhibited a marked stereospecificity. As described above, L-proline inhibited L[$^3$H]proline transport with low micromolar potency ($K_m$ approximately 9.7 µM). In contrast, D-proline only weakly inhibited transport ($K_i$ greater than 100M). A variety of proline analogs, excitatory amino acid analogs, and amino acids were tested for their ability to inhibit L-proline uptake in HeLa cells transiently transfected with pPROT (FIG. 4; Table 1; Table 2).

TABLE 1

Inhibitor Sensitivity of Proline Uptake in HeLa Cells Transfected with Rat Brain L-Proline Transporter CDNA.

| Inhibitor | $K_i$ (µM) |
| --- | --- |
| L-Pipecolic acid | 14 |
| Sarcosine | 30 |
| 3,4-Dehydroproline | 31 |
| L-Norleucine | 37 |
| L-Phenylalanine | 48 |

TABLE 1-continued

Inhibitor Sensitivity of Proline Uptake in HeLa Cells Transfected with Rat Brain L-Proline Transporter CDNA.

| Inhibitor | $K_i$ (µM) |
| --- | --- |
| L-Histidine | 83 |
| L-Cysteine | 91 |
| Azetidine-Z-carboxylic acid | 115 |

HeLa cells (100–250,000 per well) infected with T7 RNA polymerase-containing vaccinia virus were transfected with pPROT (1 g) and incubated with 50 nM L-[$^3$H]proline with or without inhibitors for 20 min. at 37° C.. $K_i$ values reflect mean estimates of triplicate determinations of uptake inhibition curves, adjusting for substrate concentration after Cheng and Prusoff (1973).

TABLE 2

Compounds with $K_i$ Values in Excess of 100 µM

Proline Analogs

L-Azetidine-2-carboxylic acid
N-acetylproline
1-Amino-1-cyclopropane carboxylic acid
3-Amino-1-hydroxy-2-pyrrolidone
Glycylproline
Hydroxyproline
D-Norleucine
(+/−)cis-2,3-piperidine dicarboxylic acid
L-Prolinamide
L-Proline methyl ester
Prolylglycine
Pyrrole-2-carboxylic acid
Excitatory Amino Acid Analogs HA-966
Ibotenic acid
Kainic acid
N-methyl-D-aspartate
Quisqualic acid
Trans-ACPD
L-Trans-2,4-PDC
Amino Acids L-Alanine
L-Arginine
L-Asparagine
D-Aspartic acid
L-Aspartic acid
L-Cystine
GABA
L-Glutamic acid
L-Glutamine
Glycine
L-Isoleucine
L-Leucine
L-Lysine
L-Methionine
D-Proline
L-Pyroglutamic acid
L-Serine
L-Threonine
L-Tryptophan
L-Tyrosine
L-Valine HeLa cells (100–250,000 per well) infected with a T7 RNA polymerase-containing vaccinia virus were transfected with pPROT (1 µg) and incubated with 50 nM L[$^3$H]proline with or without 100 µM inhibitors for 20 min at 37° C. in triplicate. Abbreviations: HA-966, 3-amino-1-hydroxy-2-pyrrolidone; L-Trans-2,4-PDC, trans-L-pyrrolidone-2,4-dicarboxylate; Trans-ACPD, trans-1-aminocyclopentane-1,3-dicarboxylic acid.

pPROT-induced L-proline transport was sensitive to pharmacological inhibition by the structurally related compounds L-pipecolic acid; sarcosine, 3,4-dehydroproline, and L-norleucine (FIG. 4), with the relative rank order of inhibition constants, $K_i$, of 14 µM, 31 µM, and 37 µM, respectively (Table 1). Of the amino acids examined, L-phenylalanine ($K_i$=48 μM), L-histidine ($K_i$=83 μM), and L-cysteine ($K_i$=91 μM) weakly inhibited L-proline uptake in transfected HeLa cells. Most L-amino acids and analogs, however, failed to inhibit high affinity L-proline transport with $K_i$ values in excess of 100 μM (Table 2). In particular, none of the excitatory amino acid analogs examined, including the specific L-glutamate uptake blocker, trans-L-pyrrolidone-2, 4-dicarboxylate (L-trans-2,4-PDC) (Bridges et al., 1991), significantly inhibited L-proline uptake.

Previous kinetic studies of L-proline uptake in rat brain synaptosomes revealed two components of transport, one with high affinity ($K_m$ =6–12 μM) and one with low affinity (Km>190 μM) (Hauptman et al., 1983, *FEBS Lett.* 161, 301–305; Nadler, 1987, *J.Neurochem.* 49, 1155–1160). High affinity L-proline transport is unique to nervous tissue In contrast, low affinity, $Na^{30}$-dependent L-proline transport has also been described in renal (Mircheff et al., 1982, *J. Membr.Biol.* 64, 113–122.; Hammerman and Sacktor, 1977, *J. Biol. Chem.* 252, 591–595) intestinal, (Stevens et al., 1984, *Annu. Rev. Physiol.* 46,417–433; Wright and Peerce, 1984, *J. Biol. Chem.* 259, 14993–14996), and choroid plexus (Ross and Wright, 1984, Res. 295, 155–160.) brush border membrane vesicles, rat brain capillaries (Hwang et al., 1983, *J. Neurochem.* 40, 317–323), and rat brain membrane vesicles (Kanner and Sharon, 1980, *Biochim. Biophys. Acta* 600, 185–194). The kinetic properties of the cloned transporter transiently expressed in HeLa cells indicate that this protein represents the high affinity L-proline transporter uniquely expressed in nervous tissue.

Several lines of evidence support a neurotransmitter or neuromodulatory role for L-proline in mammalian nervous tissue. First, regional differences in the CNS distribution of proline have been described. Second, a synaptosomal biosynthetic pathway of L-proline from ornithine has been described. Third, high affinity synaptosomal L-proline uptake exhibits a heterogeneous distribution in rodent CNS. The highest L-proline transport activities were observed in synaptosomes prepared from midbrain, caudate-putamen, hippocampus, and hypothalamus; lower activities were observed in the cerebral cortex and brain stem; and the lowest activities were observed in the cerebellum. Furthermore, high affinity, $Na^+$-dependent uptake of L-proline appears to be expressed by a subset of hippocampal glutamate pathways. Lesion studies indicated that the lateral perforant path, associational-commissural fibers in the dentate gyrus, and Schaffer collateral-commissural-ipsilateral stratum oriens fibers exhibit considerable L-proline uptake capacity; in contrast, the medial perforant path and the mossy fibers accumulate little or no L-proline. Fourth, exogenously loaded, radiolabeled L-proline is released from neocortical slices and synaptosomes in a $Ca^{2+}$-dependent manner in response to $K^+$-induced depolarization. Fifth, L-proline produces complex electrophysiological actions when iontophoresed onto neurons, producing excitatory or inhibitory actions on different types of neurons.

Many of the actions of L-proline in nervous tissue have been attributed to an interaction with excitatory glutamatergic neurotransmission. In situ hybridization results provide compelling support for a specific role for L-proline in certain excitatory pathways in the CNS. High levels of rPROT mRNA have been observed in putative glutamatergic cell bodies, including the mitral cells of the olfactory bulb, pyramidal cells of layer V of the cerebral cortex, pyramidal cells of the piriform cortex, the entorhinal cortex, and CA3 pyramidal cells of the hippocampus. In contrast, only low levels of rPROT mRNA were observed in the caudate-putamen, a brain region rich in glutamatergic nerve terminals presumably arising from glutamatergic pyramidal cells of layer V of the cerebral cortex. Based on the observation that the caudate-putamen exhibits high levels of synaptosomal L-proline transport but only low levels of rPROT mRNA, it appears that L-proline transporters are synthesized in putative glutamatergic pyramidal cells in layer V of the cerebral cortex and transported to axon terminals of these descending pathways in the caudate-putamen. The observation that rPROT mRNA is enriched in CA3 pyramidal cells of the hippocampus (see FIG. 1B) reinforces the conclusion that $Na^+$-dependent L-proline uptake is enriched in the terminal fields of the Schaffer collateral, commissural, and ipsilateral-associational projections of CA3 pyramidal cells. These neurons are believed to use an excitatory amino acid as a transmitter, and $Na^+$-dependent acidic amino acid transporters have been localized to nerve terminals of this pathway. The inability of L-glutamate, L-aspartate, and a range of structural analogs of glutamate and aspartate to inhibit L-proline transport induced by pPROT (Table 2) is consistent with the transport of L-proline and the acidic amino acids by distinct $Na^+$-dependent plasma membrane transporters that may coexist on the same synaptic terminals in subpopulations of glutamatergic neurons. The CA3-derived Schaffer collateral-commissural pathway has been implicated in associational memory processes exhibiting a robust form of long-term potentiation that is dependent upon the activation of N-methyl-D-aspartate receptors. This pathway may be the site where intracerebral injection of L-proline disrupts memory processes.

Although the presence of a high affinity, $Na^+$-dependent L-proline transporter in specific subpopulations of glutamatergic neurons is consistent with previous studies suggesting a specific postsynaptic role of L-proline at glutamate receptors, alternatives cannot be ruled out. For example, high affinity, $Na^+$-dependent 1-proline uptake could alter presynaptic handling of the excitatory transmitter glutamate. Furthermore, L-proline could serve as a precursor for glutamate, however, the enzymes that are involved in this synthesis, proline oxidase and delta-pyrroline-5-carboxylate dehydrogenase, have been found in glial cells, not neurons.

The structural features of the high affinity rat brain L-proline transporter are virtually identical to those of the other cloned $Na^+$-dependent neurotransmitter transporters, including the rat GABA, human NE, rat DA, and rat 5HT transporters. A tentative structural model for these proteins predicts the presence of approximately 12 transmembrane domains, cytoplasmic N- and C-termini, and a large, presumably glycosylated, extracellular loop separating transmembrane domains 3 and 4. Furthermore, despite dramatic differences in pharmacological sensitivities to substrates and antagonists, these transporters exhibit significant but dispersed amino acid sequence identities within or adjacent to the putative transmembrane domains. In particular, transmembrane domains 1, 2, 5, and 6 are the most well-conserved domains across the cloned transporters, exhibiting >43% amino acid sequence identity. These highly conserved transmembrane domains are likely to confer common functions to $Na^+$-dependent neurotransmitter transporters, such as the maintenance of transporter topology, ion binding, and substrate translocation. In contrast, the least well-conserved domains across the cloned transporters are the cytoplasmic N- and C-terminal tails. Furthermore, transmembrane domains 3, 4, and 9–12 are poorly conserved, exhibiting less than 20% amino acid sequence identity. These poorly conserved domains may confer substrate-specific properties to the transporters.

Although a single cDNA can induce high affinity, $Na^+$-dependent L-proline transport in transfected HeLa cells, the subunit stoichiometry of the native transporter complex has not been determined. The presence of a conserved leucine zipper motif in the second putative transmembrane domain of rPROT may mediate dimerization of proline transporter subunits in the membrane, as has been previously proposed for glucose transporters, or allow for heterotypic interactions with other membrane proteins with this motif. The ability of distinct $K^+$ channel proteins to form heteromultimeric channels with properties that are different from those of homomultimeric channels warrants the consideration of heteromultimeric neurotransmitter transporters. Recent studies suggest that second messengers may regulate the activity of $Na^+$-dependent neurotransmitter transporters. Within the putative intracellular domains of the high affinity rat brain L-proline transporter, several consensus sequences for protein kinase-mediated phosphorylation exist, and thus phosphorylation may regulate high affinity L-proline transport.

Protein can be expressed from the cDNA using standard techniques for expression in vitro in cell free translation systems, in bacteria, yeast, and animal cells, including insect, amphibian, avian, and mammalian cells, as well as genetically engineered, or transgenic, animals. The techniques are known to those skilled in the art. Reagents, including expression vectors and cell lines, for use in these methods, are commercially available from sources such as Promega and Stratagene.

It is understood that specific cDNA sequences can be modified by those skilled in the art, for example, by labelling, fusion with regulatory sequences, insertion into expression vectors, site-directed mutagenesis and substitution or deletion of nucleotides encoding specific amino/acids, without departing from the scope of the nucleotide and amino acid sequences of the present invention, and the methods for their use.

The theories and standard procedures for molecular cloning are described in *Molecular Cloning*, edited by T. Maniatis, et al. Cold Spring Harbor, Laboratory, Cold Spring Harbor, N.Y.) and are generally known to those skilled in the art. Procedures include preparation of DNA and RNA, preparation of cloning vectors, ligation, transformation of competent cells, selection and screening by in situ filter hybridization, as described by David, et al., *Advanced Bacterial Genetics* (Cold Spring Harbor Laboratory, Cold Spring, N.Y.). In addition, techniques for separation of DNA by gel electrophoresis, mapping of restriction enzyme cleavage sites, and modification of DNA fragments by modifying enzymes are used. Most restriction enzymes, vectors, and reagents can be obtained from commercial companies. Common vectors and *E. coli* strains are used, for example, pBR322, pUC series, lambda-WES, M13mp, DH5, LE392, JM109 and HB101.

Chain termination methods are used for nucleotide sequence determination to confirm the DNA constructs at the splicing sites, as reported by Sanger, et al. *Proc. Natl. Acad. Sci. USA* 74, 5463 (1977). Many commercial suppliers provide both reagent kits and detailed protocols. Since most nucleotide sequences are known for the vectors, promoters and genes to be used, oligonucleotides of defined sequences are used as primers in sequencing experiments. These are typically 15 to 20 nucleotides long and very convenient for sequencing specific regions of interest, using the techniques of Messing, et al. *Nucleic Acids Res.* 9, 309 (1981). Either single-stranded or double-stranded DNA can be sequenced with this technique.

Oliogonucleotides to be used in DNA sequencing and polymerase chain reaction are synthesized by an automated DNA synthesizer. This service can be obtained from commercial sources, such as Genetic Designs, Inc., Houston, Tex. The oligonucleotides greater than 30 nucleotides are then subjected to polyacrylamide gel electrophoresis to ensure purity.

DNAs are transfected into cells by one of several standard published procedures to form stable transformants, including, for example, calcium phosphate precipitation, DEAE-Dextran, electroporation, and protoplast fusion. These methods are described in detail as follows:

Calcium phosphate precipitation: DNAs are coprecipitated with calcium phosphate, according to the method of Graham and VanDer in *Virology* 52, 456 (1973), before transfer into cells. 40–50 µg of DNA with salmon sperm or calf thymus DNA as carrier is used for $0.5 \times 10^6$ cells plated on a 100 mm dish. DNA is mixed with 0.5 ml of 2 X Hepes solution (280 mM NaCl, 50 mM Hepes and 1.5 mM $Na_2HPO_4$, pH 7.0) to which an equal volume of $2 \times CaCl_2$ (250 mM $CaCl_2$ and 10 mM Hepes, pH 7.0) is added. A white granular precipitate appearing after 30–40 minutes is distributed dropwise evenly on the cells and allowed to sit for 4–16 hours at 37° C. The medium is removed and the cells are shocked with 15% glycerol in PBS for 3 minutes. After removing the glycerol, the cells are fed with DMEM containing 10% fetal bovine serum and left in the incubator.

Protein samples are prepared for Western blot analysis by lysing cells and separating the proteins by SDS-PAGE. The proteins are transferred to nitrocellulose by electroblotting as described by Ausubek, et al., *Current Protocols in Molecular Biology* (John Wiley and Sons, 1987). After blocking the filter with instant nonfat dry milk (1 g in 100 ml PBS), primary antibody is added to the filter and incubated for 1 h at room temperature. The filter is washed thoroughly with phosphate buffered saline (PBS) and incubated with horseradish peroxidase (HRPO)—antibody conjugate for 1 hour at room temperature. The filter is again washed thoroughly with PBS and the antigen bands are identified by adding diaminobenzidine (DAB).

Enzyme assays, protein purification, and other classical biochemical methods are employed. DNA and RNA are analyzed by Southern blotting and Northern blotting techniques. Typically, the samples to be analyzed are size fractionated by gel electrophoresis. The samples, DNA or RNA, in the gels are then transferred to nitrocellulose or nylon membranes by blotting techniques. The blots, which are replicas of sample patterns in the gels, are hybridized with probes in Southern and Northern analysis. Specific bands of interest can then be visualized by detection systems such as autoradiography.

DNA can also be transferred using the DEAE-Dextran method of Kimura, et al. *Virology* 49, 394 (1972) and Sompayrac, et al., *Proc. Natl. Acad. Sci. USA* 78, 7575 (1981); the electroporation method of Potter, *Proc. Natl. Acad. Sci. USA* 81, 7161 (1984), and the protoplast fusion method of Sandri-Goddin, et al. *Molec. Cell Biol.* 1, 743 (1981).

Construction of Transgenic Animals

The sequence provided herein can used to create transgenic animals in accordance with the method described in U.S. Pat. No. 4,873,191 to Wagner et al. Transgenic animals can also be prepared by the following method:

Animal Sources

Animals suitable for transgenic experiments can be obtained from standard commercial sources such as Charles River (Wilmington, Mass.), Taconic (Germantown, N.Y.), Harlan Sprague Dawley (Indianapolis, Ind.), etc. Swiss Webster female mice are preferred for embryo retrieval and transfer. B6D2F$_1$ males can be used for mating and vasectomized Swiss Webster studs can be used to stimulate pseudopregnancy. Vasectomized mice and rats can be obtained from the supplier.

Microinjection Procedures

The procedures for manipulation of the rodent embryo and for microinjection of DNA are described in detail in Hogan et al. Manipulating the mouse embryo, Cold Spring Harbor Labory, Cold Spring harbor, N.Y. (1986), the teachings of which are incorporated herein.

Transgenic Mice

Female mice six weeks of age are induced to superovulate with a 5 IU injection (0.1 cc, ip) of pregnant mare serum gonadotropin (PMSG; Sigma) followed 48 hours later by a 5 IU injection (0.1 cc, ip) of human chorionic gonadotropin (hCG; Sigma). Females are placed with males immediately after hCG injection. Twenty-one hours after hCG, the mated females are sacrificed by $CO_2$ asphyxiation or cervical dislocation and embryos are recovered from excised oviducts and placed in Dulbecco's phosphate buffered saline with 0.5% bovine serum albumin (BSA; Sigma). Surrounding cumulus cells are removed with hyaluronidase (1 mg/ml). Pronuclear embryos are then washed and placed in Earle's balanced salt solution containing 0.5% BSA (EBSS) in a 37.5° C. incubator with a humidified atmosphere at 5% $CO_2$, 95% air until the time of injection.

Randomly cycling adult female mice are paired with vasectomized males. Swiss Webster or other comparable strains can be used for this purpose. Recipient females are mated at the same time as donor females. At the time of embryo transfer, the recipient females are anesthetized with an intraperitoneal injection of 0.015 ml of 2.5% avertin per gram of body weight. The oviducts are exposed by a single midline dorsal incision. An incision is then made through the body wall directly over the oviduct. The ovarian bursa is then torn with watchmakers forceps. Embryos to be transferred are placed in DPBS and in the tip of a transfer pipet (about 10–12 embryos). The pipet tip is inserted into the infundibulum and the embryos transferred. After the transfer, the incision is closed by two sutures.

Transgenic Rats

The procedure for generating transgenic rats is similar to that of mice (Hammer et al., *Cell* 63;1099–112 (1990)). Thirty day-old female rats are given a subcutaneous injection of 20 IU of PMSG (0.1 cc) and 48 hours later each female placed with a proven male. At the same time, 40–80 day old females are placed in cages with vasectomized males. These will provide the foster mothers for embryo transfer. The next morning females are checked for vaginal plugs. Females who have mated with vasectomized males are held aside until the time of transfer. Donor females that have mated are sacrificed ($CO_2$ asphyxiation) and their oviducts removed, placed in DPBS (Dulbecco's phosphate buffered saline) with 0.5% BSA and the embryos collected. Cumulus cells surronding the embryos are removed with hyaluronidase (1 mg/ml). The embryos are then washed and placed in EBSS (Earle's balanced salt solution) containing 0.5% BSA in a 37.5° C. incubator until the time of microinjection.

Once the embryos are injected, the live embryos are moved to DPBS for transfer into foster mothers. The foster mothers are anesthetized with ketamine (40 mg/kg, ip) and xylazine (5 mg/kg, ip). A dorsal midline incision is made through the skin and the ovary and oviduct are exposed by an incision through the muscle layer directly over the ovary. The ovarian bursa is torn, the embryos are picked up into the transfer pipet, and the tip of the transfer pipet is inserted into the infundibulum. Approximately 10–12 embryos are transferred into each rat oviduct through the infundibulum. The incision is then closed with sutures, and the foster mothers are housed singly.

Embryonic Stem (ES) Cell Methods

Introduction of cDNA into ES cells

Methods for the culturing of ES cells and the subsequent production of transgenic animals, the introduction of DNA into ES cells by a variety of methods such as electroporation, calcium phosphate/DNA precipitation, and direct injection are described in detail in *Teratocarcinomas and embryonic stem cells, a practical approach*, ed. E. J. Robertson, (IRL Press 1987), the teachings of which are incorporated herein. Selection of the desired clone of transgene-containing ES cells is accomplished through one of several means. In cases involving random gene integration, an APP clone is co-precipitated with a gene encoding neomycin resistance. Transfection is carried out by one of several methods described in detail in Lovell-Badge, in *Teratocarcinomas and embryonic stem cells, a practical approach*, ed. E. J. Robertson, (IRL Press 1987) or in Potter et al *Proc. Natl. Acad. Sci. USA* 81, 7161 (1984). Calcium phosphate/DNA precipitation, direct injection, and electroporation are the preferred methods. In these procedures, $0.5 \times 10^6$ ES cells are plated into tissue culture dishes and transfected with a mixture of the linearized APP clone and 1 mg of pSV2neo DNA (Southern and Berg, *J. Mol Appl Gen.* 1:327–341 (1982)) precipitated in the presence of 50 mg lipofectin in a final volume of 100 μl. The cells are fed with selection medium containing 10% fetal bovine serum in DMEM supplemented with G418™ (between 200 and 500 μg/ml). Colonies of cells resistant to G418™ are isolated using cloning rings and expanded. DNA is extracted from drug resistant clones and Southern blotting experiments using an APP770 cDNA probe are used to identify those clones carrying the APP sequences. In some experiments, PCR methods are used to identify the clones of interest.

DNA molecules introduced into ES cells can also be integrated into the chromosome through the process of homologous recombination, described by Capecchi, (1989). Direct injection results in a high efficiency of integration. Desired clones are identified through PCR of DNA prepared from pools of injected ES cells. Positive cells within the pools are identified by PCR subsequent to cell cloning (Zimmer and Gruss, *Nature* 338, 150–153 (1989). DNA introduction by electroporation is less efficient and requires a selection step. Methods for positive selection of the recombination event (i.e., neo resistance) and dual positive-negative selection (i.e., neo resistance and gancyclovir resistance) and the subsequent identification of the desired clones by PCR have been described by Joyner et al., *Nature* 338, 153–156 (1989) and Capecchi, (1989), the teachings of which are incorporated herein.

Embryo Recovery and ES cell Injection

Naturally cycling or superovulated female mice mated with males are used to harvest embryos for the implantation of ES cells. It is desirable to use the C57B strain for this purpose when using mice. Embryos of the appropriate age are recovered approximately 3.5 days after successful mating. Mated females are sacrificed by $CO_2$ asphyxiation or cervical dislocation and embryos are flushed from excised uterine horns and placed in Dulbecco's modified essential medium plus 10% calf serum for injection with ES cells. Approximately 10–20 ES cells are injected into blastocysts using a glass microneedle with an internal diameter of approximately 20 μm.

Transfer of Embryos to Pseudopregnant Females

Randomly cycling adult female mice are paired with vasectomized males. Mouse strains such as Swiss Webster, ICR or others can be used for this purpose. Recipient females are mated such that they will be at 2.5 to 3.5 days post-mating when required for implantation with blastocysts containing ES cells. At the time of embryo transfer, the recipient females are anesthetized with an intraperitoneal injection of 0.015 ml of 2.5% avertin per gram of body weight. The ovaries are exposed by making an incision in the body wall directly over the oviduct and the ovary and uterus are externalized. A hole is made in the uterine horn with a 25 guage needle through which the blastocysts are transferred. After the transfer, the ovary and uterus are pushed back into the body and the incision is closed by two sutures. This procedure is repeated on the opposite side if additional transfers are to be made.

Identification of Transqenic Mice and Rats

Tail samples (1–2 cm) are removed from three week old animals. DNA is prepared and analyzed by both Southern blot and PCR to detect transgenic founder ($F_0$) animals and their progeny ($F_1$ and $F_2$).

Transgenic animal prepared by these methods can be used for in vivo tests. This transgenic model allows simple and easy screening for pharmacologic agents capable of enhancing or decreasing levels of L-proline in brain synapses in vivo.

The sequence provided herein can also be used as a hybridization probe when labelled with a fluorescent or radiolabelled nucleotide. Probes can also be labelled using dyes, or enzymatic or chemiluminescent labels that are commercially available. These probes can be used to detect the expression of the high affinity L-proline transporter or related sequences in cells, tissue samples, or in in vitro reagents, as well as to screen samples from humans suspected of having an L-proline transporter disease or disorder. Levels of gene expression can be quantitated in patients and compared to healthy controls, or can be compared between different tissues.

The sequence provided herein encoding the high affinity L-proline transporter can be specifically used to isolate the sequence from other species, especially human.

The sequence provided herein can also be used to screen for compounds that modulate the expression or transport of proline by the transporter. The sequence can also be used to screen for compounds that bind directly to the high affinity L-proline transporter permitting its localization in situ and to screen for compounds that directly or indirectly interfere with L-proline transport. Compounds can be developed by conventional computer modelling methods as described below.

Computer Modeling

Computer modeling technology allows visualization of the three-dimensional atomic structure of a selected molecule and the rational design of new compounds that will interact with the transporter molecule. The three-dimensional construct typically depends on data from x-ray crystallographic analyses or NMR imaging of the selected molecule. The molecular dynamics require force field data. The computer graphics systems enable prediction of how a new compound will link to the target molecule and allow experimental manipulation of the structures of the compound and target molecule to perfect binding specificity. Prediction of what the molecule-compound interaction will be when small changes are made in one or both requires molecular mechanics software and computationally intensive computers, usually coupled with user-friendly, menu-driven interfaces between the molecular design program and the user.

An example of the molecular modelling system described generally above consists of the CHARMm and QUANTA programs, Polygen Corporation, Waltham, Mass. CHARMm performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modeling of drugs interactive with specific proteins, such as Rotivinen, et al., *Acta Pharmaceutica Fennica* 97, 159–166 (1988); Ripka, *New Scientist* 54–57 (Jun. 16, 1988); McKinaly and Rossmann, *Annu. Rev. Pharmacol. Toxiciol.* 29, 111–122 (1989); Perry and Davies, *QSAR: Quantitative Structure-Activity Relationships in Drug Design* pp. 189–193 (Alan R. Liss, Inc. 1989); Lewis and Dean, *Proc. R. Soc. Lond.* 236, 125–140 and 141–162 (1989); and, with respect to a model receptor for nucleic acid components, Askew, et al., *J. Am. Chem. Soc.* 111, 1082–1090 (1989).

Computer modelling has found limited use in the design of compounds that will interact with nucleic acids, because the generation of force field data and x-ray crystallographic information has lagged behind computer technology. CHARMm has been used for visualization of the three-dimensional structure of parts of four RNAs, as reported by Mei, et al., *Proc. Natl. Acad. Sci.* 86:9727 (1989), but computer modelling has not been used to design compounds that will bind to and inactivate RNA.

Other computer programs that screen and graphically depict chemicals are available from companies such as BioDesign, Inc., Pasadena, Calif., Allelix, Inc, Mississauga, Ontario, Canada, and Hypercube, Inc., Cambridge, Ontario. Although these are primarily designed for application to drugs specific to particular proteins, they can be adapted to design of drugs specific to regions of RNA, once that region is identified.

Synthesis of transporter modulating compounds

Compounds which specifically inhibit the function of the transporter molecule are synthesized using methods known to those skilled in the art based on the sequence and structure determined as described above. Known compounds can also be modified or selected on the basis of their existing structure, once the requirements for specificity are known.

The compounds can be organic, inorganic, proteins, or even other nucleic acids. Specific binding to the targeted molecule can be achieved by including in the molecule complementary nucleic acid sequence that forms base pairs with the transporter sequence under appropriate conditions, or by inclusion of chemical groups having the correct spatial location and charge.

In the preferred embodiments, compounds are designed as a peptide or organic compound with hydrogen bond donor and acceptor sites arranged to be complementary to the cDNA.

For peptides, the proposed hydrogen acceptors are the carbonyl oxygens of the peptide backbone; the side chains of glutamic acid, aspartic acid, asparagine, glutamine; and the imidazole nitrogen of histidine. The proposed hydrogen bond donors are the backbone amides N—H; the side chain hydroxyl groups of serine, threonine, and tyrosine; the sulfhydryl of cysteine; the indole of N—H of tryptophan; the guanidino group of arginine; the $NH_2$ of glutamine and asparagine; and the N—H of imidazole side chain of histidine.

A peptide is formed with the amino acids ordered to yield the correct spatial arrangement of hydrogen bond acceptors and donors, when the peptide is in a specific conformation induced and stabilized by binding to the target cDNA segment. The likelihood of forming the desired conformation can be refined and/or optimized using molecular computational programs.

Organic compounds can be designed to be rigid, or to present hydrogen bonding groups on edge or plane, which can interact with complementary sites. Rebek, *Science* 235, 1478–1484 (1987) and Rebek, et al., *J. Am. Chem. Soc.* 109, 2426–2431 (1987), have summarized some of these approaches and the mechanisms involved in binding of compounds to regions of proteins.

In some cases, the inhibitory compound is a nucleic acid molecule, either RNA or DNA. This can be prepared synthetically using commercially available equipment or by cloning of an appropriate sequence which is designed or derived from the sequence to be inhibited.

The methods, reagents, and computer software programs described in the references cited herein are specifically incorporated by reference. Other methods and materials useful for molecular modeling and chemical synthesis are known to those skilled in the art.

Antibodies

Expressed protein can also be used to immunize animals to generate polyclonal antisera and/or monoclonal antibodies useful in detection and localization of the transporter in accordance with methods well known to those skilled in the art.

Modifications and variations of the present invention, nucleic acid sequence encoding a high affinity, $Na^+$-dependent L-proline transporter, and the encoded protein, as well as methods of use thereof, will be obvious to those skilled in the art from the foregoing detailed description. Such modifications and variations are intended to come within the scope of the appended claims.

We claim:

1. An isolated nucleic acid molecule encoding a high-affinity, $Na^+$-dependent L-proline transporter expressed in mammalian brain, wherein the molecule hybridizes under standard conditions to a nucleic acid molecule complementary to the full length of SEQ ID NO: 7.

2. The molecule of claim 1 comprising SEQ ID NO:7.

3. The molecule of claim 1 further comprising a label for detection.

4. A vector for expression in host cells in culture comprising the molecule of claim 1.

5. A host cell selected from the group consisting of procaryotic, yeast, and mammalian cells, wherein the cell is transformed with the vector of claim 4.

6. An isolated nucleic acid molecule having the sequence of a portion of the nucleic acid molecule of claim 1, said portion comprising a sequence corresponding to a domain of said transporter, wherein said domain is selected from the group consisting of the cytoplasmic N-terminal tail, the cytoplasmic C-terminal tail, and transmembrane domains 3, 4, 9, 10, 11, and 12.

7. The molecule of claim 6 further comprising a label for detection.

8. An isolated DNA sequence comprising a sequence encoding a high-affinity, $Na^+$-dependent L-proline transporter expressed in mammalian brain, said transporter comprising the amino acid sequence shown in SEQ ID NO: 8.

* * * * *

SEQUENCE LISTING ( 1 ) GENERAL INFORMATION:

( i i i ) NUMBER OF SEQUENCES: 13

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
        ( A ) ORGANISM: Rattus ( i x ) FEATURE:
        ( A ) NAME/KEY: Domain
        ( B ) LOCATION: 1..7
        ( D ) OTHER INFORMATION: /note="Synthetic degenerate
            oligonucleotide primer"

( x i ) SEQUENCE DESCRIPTION: SEQ ID NO:1:

Asn   Val   Trp   Arg   Phe   Pro   Tyr
    1                           5

( 2 ) INFORMATION FOR SEQ ID NO:2:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( i i i ) HYPOTHETICAL: NO ( i v ) ANTI-SENSE: NO ( v i ) ORIGINAL SOURCE:
        ( A ) ORGANISM: Rattus ( i x ) FEATURE:

(A) NAME/KEY: Domain
            (B) LOCATION: 1..7
            (D) OTHER INFORMATION: /note="Synthetic degenerate
                oligonucleotide primer"

(xi) SEQUENCE DESCRIPTION: SEQ ID NO:2:

Trp  Ile  Asp  Ala  Ala  Thr  Gln
    1                 5

(2) INFORMATION FOR SEQ ID NO:3:

(i) SEQUENCE CHARACTERISTICS:
            (A) LENGTH: 29 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Rattus (ix) FEATURE:
            (A) NAME/KEY: misc_feature
            (B) LOCATION: 1..29
            (D) OTHER INFORMATION: /note="Synthetic, degenerate
                oligonucleotide"

(xi) SEQUENCE DESCRIPTION: SEQ ID NO:3:

CCGCTCGAGA AYGTSTGGCG STTYCCNTA                29

(2) INFORMATION FOR SEQ ID NO:4:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Rattus
            (F) TISSUE TYPE: Brain (ix) FEATURE:
            (A) NAME/KEY: misc_feature
            (B) LOCATION: 1..30
            (D) OTHER INFORMATION: /note="Synthetic, degenerate
                oligonucleotide"

(ix) FEATURE:
            (A) NAME/KEY: misc_feature
            (B) LOCATION: 16..17
            (D) OTHER INFORMATION: /note="N at position 16 identifies
                Inosine."

(xi) SEQUENCE DESCRIPTION: SEQ ID NO:4:

GCTCTAGAGC TGRGTNGCRC CRTCRAKCCA                30

(2) INFORMATION FOR SEQ ID NO:5:

(i) SEQUENCE CHARACTERISTICS:
            (A) LENGTH: 22 base pairs
            (B) TYPE: nucleic acid
            (C) STRANDEDNESS: single (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Rattus (vii) IMMEDIATE SOURCE:
        (B) CLONE: PCR fragment rTB2-2

(ix) FEATURE:
        (A) NAME/KEY: misc_feature
        (B) LOCATION: 1..22
        (D) OTHER INFORMATION: /note="Oligonucleotide"

(xi) SEQUENCE DESCRIPTION: SEQ ID NO:5:

```
AACGGTGGCG CTTTCCTTAT CG                                              22
```

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: YES (vii) IMMEDIATE SOURCE:
        (B) CLONE: PCR fragment rTB2-2

(ix) FEATURE:
        (A) NAME/KEY: misc_feature
        (B) LOCATION: 1..21
        (D) OTHER INFORMATION: /note="Oligonucleotide"

(xi) SEQUENCE DESCRIPTION: SEQ ID NO:6:

```
TGCACCCGCA CCTTTGAAGA G                                               21
```

(2) INFORMATION FOR SEQ ID NO:7:

(i) SEQUENCE CHARACTERISTICS:
        (A) LENGTH: 2728 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Rattus
        (F) TISSUE TYPE: Brain (vii) IMMEDIATE SOURCE:
        (A) LIBRARY: rat forebrain cDNA library
        (B) CLONE: rTB2-2-20

(xi) SEQUENCE DESCRIPTION: SEQ ID NO:7:

```
TATCTCAAAG GCGCAGAGAT AGGACCAGTG CTCGGCGCCC GCTTGGCTGG CTGACTGCGC      60

TCTTGCAAGC ACCGGTGCCA GCTCTCCAAG ATGAAGAAGC TCCAGGAAGC TCACCTCCGC     120

AAGCCTGTCA CCCCAGACCT GCTGATGACT CCCAGTGACC AGGGTGATGT GGACCTGGAT     180
```

-continued

| | | | | | |
|---|---|---|---|---|---|
| GTAGACTTTG | CAGCAGACAG | AGGCAACTGG | ACGGGCAAGC | TGGACTTCTT | GCTGTCCTGC | 240 |
| ATCGGCTACT | GTGTGGGCTT | GGGAAATGTC | TGGCGGTTTC | CCTATCGAGC | CTACACCAAT | 300 |
| GGAGGCGGAG | CCTTCCTCGT | GCCCTACTTC | CTCATGCTGG | CCATCTGTGG | CATCCCCCTC | 360 |
| TTCTTTCTTG | AGCTCTCCCT | GGGCCAGTTC | TCCAGCCTGG | ACCCCTGGC | TGTCTGGAAA | 420 |
| ATCAGCCCCC | TCTTCAAAGG | TGCGGGTGCA | GCCATGCTGC | TCATCGTGGG | CCTGGTGGCC | 480 |
| ATCTACTACA | ACATGATCAT | CGCCTACGTC | CTCTTCTACC | TCTTCGCCTC | CCTCACCAGC | 540 |
| AACCTGCCCT | GGGAGCATTG | CGGCAACTGG | TGGAACACAG | AACGCTGCCT | GGAGCACAGA | 600 |
| GGCCCCAAGG | ATGGCAACGG | GCACTGCCT | CTTAACCTCA | GCAGCACTGT | CAGCCCCAGT | 660 |
| GAGGAGTACT | GGAGCCGATA | TGTCCTGCAC | ATTCAGGGCA | GCCAGGGCAT | CGGCCGACCC | 720 |
| GGGGAGATTC | GCTGGAACCT | CTGCCTCTGC | CTGCTGCTGG | CCTGGGTCAT | CGTGTTTCTC | 780 |
| TGTATCCTGA | AGGGGGTGAA | GTCCTCGGGC | AAGGTGGTGT | ATTTCACAGC | CACCTTTCCC | 840 |
| TACCTCATCC | TGCTCATGCT | CCTGGTTCGA | GGAGTGACCC | TTCCCGGGGC | CTGGAAGGGC | 900 |
| ATCCAGTTCT | ATCTCACCCC | CCAATTCCAC | CACCTGCTGT | CTTCCAAGGT | GTGGATTGAA | 960 |
| GCTGCTCTTC | AGATCTTCTA | CTCTCTAGGA | GTGGGTTTTG | GGGTCTTCT | CACCTTTGCC | 1020 |
| TCCTACAACA | CATTCCACCA | GAACATCTAC | AGAGACACCT | TCATTGTCAC | TCTGGGCAAT | 1080 |
| GCCATCACCA | GCATCCTGGC | TGGTTTTGCT | ATCTTCTCGG | TGCTGGGCTA | CATGTCGCAG | 1140 |
| GAGCTGGGTG | TGCCTGTGGA | CCAAGTGGCC | AAAGCAGGCC | CTGGCCTGGC | CTTTGTTATC | 1200 |
| TACCCACAGG | CCATGACTAT | GTTGCCTCTG | TCACCCTTCT | GGTCCTTCCT | CTTCTTCTTC | 1260 |
| ATGCTTCTGA | CTCTTGGCCT | CGATAGCCAG | TTTGCCTTTC | TGGAAACCAT | AGTGACTGCA | 1320 |
| GTGACCGATG | AGTTCCCATA | CTACCTACGG | CCCAAGAAGG | CAGTGTTCTC | AGGCCTCATC | 1380 |
| TGTGTAGCCA | TGTACCTGAT | GGGACTGATC | CTCACCACCG | ATGGGGGGAT | GTACTGGCTG | 1440 |
| GTCCTTCTGG | ATGACTACAG | CGCCAGCTTC | GGACTCATGG | TGGTGGTGAT | TACCACATGC | 1500 |
| CTCGCTGTCA | CCCGGGTATA | CGGCATCCAG | CGGTTTTGTC | GTGACATCCA | CATGATGCTG | 1560 |
| GGCTTCAAGC | CAGGACTCTA | CTTCAGGGCC | TGCTGGCTGT | TTTGTCTCC | GGCCACACTC | 1620 |
| TTGGCCTTGC | TGGTGTACAG | TATCGTCAAG | TACCAGCCCT | CGGAATACGG | TAGCTATCGC | 1680 |
| TTCCCCGCCT | GGGCCGAGCT | GCTAGGCATC | CTGATGGGCC | TGCTCTCCTG | CCTCATGATC | 1740 |
| CCAGCTGGCA | TGCTGGTAGC | TGTGCTTCGA | GAGGAGGGCT | CGCTCTGGGA | GCGACTTCAG | 1800 |
| CAAGCCAGCC | GTCCTGCTAT | AGACTGGGGC | CCATCACTGG | AAGAGAACCG | GACGGGCATG | 1860 |
| TATGTGGCCA | CCCTGGCTGG | GAGCCAGTCA | CCAAAACCAC | TGATGGTACA | CATGCGAAAA | 1920 |
| TATGGGGGCA | TCACCAGCTT | CGAGAATACA | GCCATTGAGG | TGGACCGTGA | GATCGCAGAG | 1980 |
| GAGGAAGAGG | AGTCCATGAT | GTGAGACCAG | ACACCTCCAA | ACAGGAGGGC | TGGTCGGGGC | 2040 |
| CTCCCCGTCT | GTCCCTTCCT | TGGCCACAGG | GGATAGCTTT | GTCTGTTGGG | ATTCTGACAG | 2100 |
| GCAATGGGAG | GTTGCCATGG | CAACGACAGT | CCCCAGCCTA | AGTCCCTCTT | TGTGGCCTCT | 2160 |
| ACATCTCCTG | GAACCTCTAG | ATGGACATAC | ATATACTAGG | TAACCCATTC | AAAGCTGAAA | 2220 |
| CGATTCAGCT | CAGCCCTCAG | TTTGTGAGGG | GGTGCGTTGA | AGCCAGGGAG | AGAAGAGCTG | 2280 |
| GACCAAGGTG | ACATGCCCAA | GAGGACTTGT | TCCCAAGCCT | CCTCCAGCCA | GTCAACTCCC | 2340 |
| TTTCCCTTGG | GGGAGCAAGC | ACCATATCTG | ACATCTTTGT | TCAGACACTT | TGACAAGATA | 2400 |
| CATTTCCATA | CAAGCCAACT | TTAAACCCCA | GGTTCAGGGT | AGCGAGAACC | TGGAGAGCCC | 2460 |
| CAAGGCCCTG | GATATAGATA | GAATGGCAGC | GACCAAATTG | GGTAGAAAAG | TCTTTGTGGG | 2520 |
| TTCCTGTGTT | AAGGCCAGTT | TTCCCAGAAG | AAGTGGGAGC | TTTAGGGCTG | AGAGGTGTGA | 2580 |

| | | | | | | |
|---|---|---|---|---|---|---|
| AAGATTGCAG | AAGAGGCTAG | AGGGAAGGTT | TGCGGGTCAG | AGCTGCCCCT | GAGCCAGGAG | 2640 |
| GAGGCCCAAC | CTGCCAGAGC | AGAGACCAGG | AGGGGCTGGA | GATTGTGGTG | CTCCCGGGTT | 2700 |
| ATGAGAGGGA | ATAAAGACTC | GCAGGGCC | | | | 2728 |

( 2 ) INFORMATION FOR SEQ ID NO:8:

( i ) SEQUENCE CHARACTERISTICS:
        ( A ) LENGTH: 667 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Rattus
        ( F ) TISSUE TYPE: Brain ( v i i ) IMMEDIATE SOURCE:
        ( A ) LIBRARY: rat forebrain cDNA library
        ( B ) CLONE: rTB2-2-20

( i x ) FEATURE:
        ( A ) NAME/KEY: Domain
        ( B ) LOCATION: 76..95
        ( D ) OTHER INFORMATION: /note="Membrane-spanning domain"

( i x ) FEATURE:
        ( A ) NAME/KEY: Domain
        ( B ) LOCATION: 103..127
        ( D ) OTHER INFORMATION: /note="Membrane-spanning domain"

( i x ) FEATURE:
        ( A ) NAME/KEY: Domain
        ( B ) LOCATION: 147..167
        ( D ) OTHER INFORMATION: /note="Membrane-spanning domain"

( i x ) FEATURE:
        ( A ) NAME/KEY: Domain
        ( B ) LOCATION: 247..266
        ( D ) OTHER INFORMATION: /note="Membrane-spanning domain"

( i x ) FEATURE:
        ( A ) NAME/KEY: Domain
        ( B ) LOCATION: 272..294
        ( D ) OTHER INFORMATION: /note="Membrane-spanning domain"

( i x ) FEATURE:
        ( A ) NAME/KEY: Domain
        ( B ) LOCATION: 321..341
        ( D ) OTHER INFORMATION: /note="Membrane-spanning domain"

( i x ) FEATURE:
        ( A ) NAME/KEY: Domain
        ( B ) LOCATION: 353..375
        ( D ) OTHER INFORMATION: /note="Membrane-spanning domain"

( i x ) FEATURE:
        ( A ) NAME/KEY: Domain
        ( B ) LOCATION: 404..427
        ( D ) OTHER INFORMATION: /note="Membrane-spanning domain"

( i x ) FEATURE:
        ( A ) NAME/KEY: Domain
        ( B ) LOCATION: 454..473
        ( D ) OTHER INFORMATION: /note="Membrane-spanning domain"

( i x ) FEATURE:
        ( A ) NAME/KEY: Domain
        ( B ) LOCATION: 487..509

(D) OTHER INFORMATION: /note="Membrane-spanning domain"

(ix) FEATURE:
    (A) NAME/KEY: Domain
    (B) LOCATION: 530..549
    (D) OTHER INFORMATION: /note="Membrane-spanning domain"

(ix) FEATURE:
    (A) NAME/KEY: Domain
    (B) LOCATION: 567..589
    (D) OTHER INFORMATION: /note="Membrane-spanning domain"

(ix) FEATURE:
    (A) NAME/KEY: Region
    (B) LOCATION: 44..45
    (D) OTHER INFORMATION: /note="protein kinase C phosphorylation site"

(ix) FEATURE:
    (A) NAME/KEY: Region
    (B) LOCATION: 71..72
    (D) OTHER INFORMATION: /note="cAMP-dependent protein kinase phosphorylation site"

(ix) FEATURE:
    (A) NAME/KEY: Region
    (B) LOCATION: 269..270
    (D) OTHER INFORMATION: /note="protein kinase C phosphorylation site"

(ix) FEATURE:
    (A) NAME/KEY: Region
    (B) LOCATION: 630..631
    (D) OTHER INFORMATION: /note="protein kinase C phosphorylation site"

(ix) FEATURE:
    (A) NAME/KEY: Region
    (B) LOCATION: 106..127
    (D) OTHER INFORMATION: /note="Leucine zipper motif"

(ix) FEATURE:
    (A) NAME/KEY: Region
    (B) LOCATION: 212..213
    (D) OTHER INFORMATION: /note="N-linked glycosylation site"

(xi) SEQUENCE DESCRIPTION: SEQ ID NO:8:

```
Pro Arg Leu Ile Asn Glu Thr Arg Ala Asn Ser Pro Arg Thr Glu Arg
 1               5                  10                  15

Pro Glu Pro Thr Ile Asp Glu Ser Glu Gln Glu Asn Cys Glu Met Lys
                20                  25                  30

Lys Leu Gln Glu Ala His Leu Arg Lys Pro Val Thr Pro Asp Leu Leu
            35                  40                  45

Met Thr Pro Ser Asp Gln Gly Asp Val Asp Leu Asp Val Asp Phe Ala
        50                  55                  60

Ala Asp Arg Gly Asn Trp Thr Gly Lys Leu Asp Phe Leu Leu Ser Cys
65                  70                  75                  80

Ile Gly Tyr Cys Val Gly Leu Gly Asn Val Trp Arg Phe Pro Tyr Arg
                85                  90                  95

Ala Tyr Thr Asn Gly Gly Gly Ala Phe Leu Val Pro Tyr Phe Leu Met
               100                 105                 110

Leu Ala Ile Cys Gly Ile Pro Leu Phe Phe Leu Glu Leu Ser Leu Gly
           115                 120                 125

Gln Phe Ser Ser Leu Gly Pro Leu Ala Val Trp Lys Ile Ser Pro Leu
       130                 135                 140

Phe Lys Gly Ala Gly Ala Ala Met Leu Leu Ile Val Gly Leu Val Ala
145                 150                 155                 160

Ile Tyr Tyr Asn Met Ile Ile Ala Tyr Val Leu Phe Tyr Leu Phe Ala
```

```
                              165                    170                    175
Ser  Leu  Thr  Ser  Asn  Leu  Pro  Trp  Glu  His  Cys  Gly  Asn  Trp  Trp  Asn
              180                    185                    190

Thr  Glu  Arg  Cys  Leu  Glu  His  Arg  Gly  Pro  Lys  Asp  Gly  Asn  Gly  Ala
              195                    200                    205

Leu  Pro  Leu  Asn  Leu  Ser  Ser  Thr  Val  Ser  Pro  Ser  Glu  Glu  Tyr  Trp
     210                    215                    220

Ser  Arg  Tyr  Val  Leu  His  Ile  Gln  Gly  Ser  Gln  Gly  Ile  Gly  Arg  Pro
225                      230                    235                         240

Gly  Glu  Ile  Arg  Trp  Asn  Leu  Cys  Leu  Cys  Leu  Leu  Leu  Ala  Trp  Val
               245                         250                    255

Ile  Val  Phe  Leu  Cys  Ile  Leu  Lys  Gly  Val  Lys  Ser  Ser  Gly  Lys  Val
               260                    265                    270

Val  Tyr  Phe  Thr  Ala  Thr  Phe  Pro  Tyr  Leu  Ile  Leu  Leu  Met  Leu  Leu
          275                    280                    285

Val  Arg  Gly  Val  Thr  Leu  Pro  Gly  Ala  Trp  Lys  Gly  Ile  Gln  Phe  Tyr
          290                    295                    300

Leu  Thr  Pro  Gln  Phe  His  His  Leu  Leu  Ser  Ser  Lys  Val  Trp  Ile  Glu
305                      310                    315                         320

Ala  Ala  Leu  Gln  Ile  Phe  Tyr  Ser  Leu  Gly  Val  Gly  Phe  Gly  Gly  Leu
                    325                    330                         335

Leu  Thr  Phe  Ala  Ser  Tyr  Asn  Thr  Phe  His  Gln  Asn  Ile  Tyr  Arg  Asp
               340                    345                    350

Thr  Phe  Ile  Val  Thr  Leu  Gly  Asn  Ala  Ile  Thr  Ser  Ile  Leu  Ala  Gly
          355                    360                    365

Phe  Ala  Ile  Phe  Ser  Val  Leu  Gly  Tyr  Met  Ser  Gln  Glu  Leu  Gly  Val
     370                    375                    380

Pro  Val  Asp  Gln  Val  Ala  Lys  Ala  Gly  Pro  Gly  Leu  Ala  Phe  Val  Ile
385                      390                    395                         400

Tyr  Pro  Gln  Ala  Met  Thr  Met  Leu  Pro  Leu  Ser  Pro  Phe  Trp  Ser  Phe
               405                    410                    415

Leu  Phe  Phe  Phe  Met  Leu  Leu  Thr  Leu  Gly  Leu  Asp  Ser  Gln  Phe  Ala
               420                    425                    430

Phe  Leu  Glu  Thr  Ile  Val  Thr  Ala  Val  Thr  Asp  Glu  Phe  Pro  Tyr  Tyr
          435                    440                    445

Leu  Arg  Pro  Lys  Lys  Ala  Val  Phe  Ser  Gly  Leu  Ile  Cys  Val  Ala  Met
     450                    455                    460

Tyr  Leu  Met  Gly  Leu  Ile  Leu  Thr  Thr  Asp  Gly  Gly  Met  Tyr  Trp  Leu
465                      470                    475                         480

Val  Leu  Leu  Asp  Asp  Tyr  Ser  Ala  Ser  Phe  Gly  Leu  Met  Val  Val  Val
               485                    490                    495

Ile  Thr  Thr  Cys  Leu  Ala  Val  Thr  Arg  Val  Tyr  Gly  Ile  Gln  Arg  Phe
               500                    505                    510

Cys  Arg  Asp  Ile  His  Met  Met  Leu  Gly  Phe  Lys  Pro  Gly  Leu  Tyr  Phe
          515                    520                    525

Arg  Ala  Cys  Trp  Leu  Phe  Leu  Ser  Pro  Ala  Thr  Leu  Leu  Ala  Leu  Leu
     530                    535                    540

Val  Tyr  Ser  Ile  Val  Lys  Tyr  Gln  Pro  Ser  Glu  Tyr  Gly  Ser  Tyr  Arg
545                      550                    555                         560

Phe  Pro  Ala  Trp  Ala  Glu  Leu  Leu  Gly  Ile  Leu  Met  Gly  Leu  Leu  Ser
               565                    570                    575

Cys  Leu  Met  Ile  Pro  Ala  Gly  Met  Leu  Val  Ala  Val  Leu  Arg  Glu  Glu
               580                    585                    590
```

| Gly | Ser | Leu | Trp | Glu | Arg | Leu | Gln | Gln | Ala | Ser | Arg | Pro | Ala | Ile | Asp |
|  |  | 595 |  |  |  |  | 600 |  |  |  |  | 605 |  |  |  |

| Trp | Gly | Pro | Ser | Leu | Glu | Glu | Asn | Arg | Thr | Gly | Met | Tyr | Val | Ala | Thr |
|  | 610 |  |  |  | 615 |  |  |  |  | 620 |  |  |  |  |  |

| Leu | Ala | Gly | Ser | Gln | Ser | Pro | Lys | Pro | Leu | Met | Val | His | Met | Arg | Lys |
| 625 |  |  |  |  | 630 |  |  |  |  | 635 |  |  |  |  | 640 |

| Tyr | Gly | Gly | Ile | Thr | Ser | Phe | Glu | Asn | Thr | Ala | Ile | Glu | Val | Asp | Arg |
|  |  |  |  | 645 |  |  |  |  | 650 |  |  |  |  | 655 |  |

| Glu | Ile | Ala | Glu | Glu | Glu | Glu | Glu | Ser | Met | Met |
|  |  |  | 660 |  |  |  |  | 665 |  |  |

(2) INFORMATION FOR SEQ ID NO:9:

(i) SEQUENCE CHARACTERISTICS:
        (A) LENGTH: 635 amino acids
        (B) TYPE: amino acid
        (C) STRANDEDNESS: single
        (D) TOPOLOGY: linear (i i) MOLECULE TYPE: protein (i i i) HYPOTHETICAL: NO (i v) ANTI-SENSE: NO (v) FRAGMENT TYPE: N-terminal (v i) ORIGINAL SOURCE:
        (A) ORGANISM: Rattus
        (F) TISSUE TYPE: Brain - Proline Transporter (i x) FEATURE:
        (A) NAME/KEY: Domain
        (B) LOCATION: 46..65
        (D) OTHER INFORMATION: /note="Proposed transmembrane
            domain."

(i x) FEATURE:
        (A) NAME/KEY: Domain
        (B) LOCATION: 72..97
        (D) OTHER INFORMATION: /note="Proposed transmembrane
            domain."

(i x) FEATURE:
        (A) NAME/KEY: Domain
        (B) LOCATION: 117..137
        (D) OTHER INFORMATION: /note="Proposed transmembrane
            domain."

(i x) FEATURE:
        (A) NAME/KEY: Domain
        (B) LOCATION: 217..236
        (D) OTHER INFORMATION: /note="Proposed transmembrane
            domain."

(i x) FEATURE:
        (A) NAME/KEY: Domain
        (B) LOCATION: 243..264
        (D) OTHER INFORMATION: /note="Proposed transmembrane
            domain."

(i x) FEATURE:
        (A) NAME/KEY: Domain
        (B) LOCATION: 291..311
        (D) OTHER INFORMATION: /note="Proposed transmembrane
            domain."

(i x) FEATURE:
        (A) NAME/KEY: Domain
        (B) LOCATION: 322..345
        (D) OTHER INFORMATION: /note="Proposed transmembrane
            domain."

(i x) FEATURE:
        (A) NAME/KEY: Domain (B) LOCATION: 373..397
(D) OTHER INFORMATION: /note="Proposed transmembrane domain."

(ix) FEATURE:
(A) NAME/KEY: Domain
(B) LOCATION: 424..443
(D) OTHER INFORMATION: /note="Proposed transmembrane domain."

(ix) FEATURE:
(A) NAME/KEY: Domain
(B) LOCATION: 456..479
(D) OTHER INFORMATION: /note="Proposed transmembrane domain."

(ix) FEATURE:
(A) NAME/KEY: Domain
(B) LOCATION: 500..519
(D) OTHER INFORMATION: /note="Proposed transmembrane domain."

(ix) FEATURE:
(A) NAME/KEY: Domain
(B) LOCATION: 536..559
(D) OTHER INFORMATION: /note="Proposed transmembrane domain."

(ix) FEATURE:
(A) NAME/KEY: Active-site
(B) LOCATION: 76..77
(D) OTHER INFORMATION: /note="Leucine zipper motif"

(ix) FEATURE:
(A) NAME/KEY: Active-site
(B) LOCATION: 83..84
(D) OTHER INFORMATION: /note="Leucine zipper motif"

(ix) FEATURE:
(A) NAME/KEY: Active-site
(B) LOCATION: 90..91
(D) OTHER INFORMATION: /note="Leucine zipper motif"

(ix) FEATURE:
(A) NAME/KEY: Active-site
(B) LOCATION: 97..98
(D) OTHER INFORMATION: /note="Leucine zipper motif"

(xi) SEQUENCE DESCRIPTION: SEQ ID NO:9:

```
Met Lys Lys Leu Gln Glu Ala His Leu Arg Lys Pro Val Thr Pro Asp
 1               5                  10                  15

Leu Leu Met Thr Pro Ser Asp Gln Gly Asp Val Asp Leu Asp Val Asp
            20                  25                  30

Phe Ala Ala Asp Arg Gly Asn Trp Thr Gly Lys Leu Asp Phe Leu Leu
            35                  40                  45

Ser Cys Ile Gly Tyr Cys Val Gly Leu Gly Asn Val Trp Arg Phe Pro
    50                  55                  60

Tyr Arg Ala Tyr Thr Asn Gly Gly Gly Ala Phe Leu Val Pro Tyr Phe
65                  70                  75                  80

Leu Met Leu Ala Ile Cys Gly Ile Pro Leu Phe Phe Leu Glu Leu Ser
            85                  90                  95

Leu Gly Gln Phe Ser Ser Leu Gly Pro Leu Ala Val Trp Lys Ile Ser
            100                 105                 110

Pro Leu Phe Lys Gly Ala Gly Ala Ala Met Leu Leu Ile Val Gly Leu
            115                 120                 125

Val Ala Ile Tyr Tyr Asn Met Ile Ile Ala Tyr Val Leu Phe Tyr Leu
    130                 135                 140

Phe Ala Ser Leu Tyr Ser Asn Leu Pro Trp Glu His Cys Gly Asn Trp
145                 150                 155                 160
```

-continued

| | | | | | | | | | | | | | |
|---|---|---|---|---|---|---|---|---|---|---|---|---|---|
| Trp | Asn | Thr | Glu | Arg<br>165 | Cys | Leu | Glu | His | Arg<br>170 | Gly | Pro | Lys | Asp | Gly | Asn<br>175 |
| Gly | Ala | Leu | Pro<br>180 | Leu | Asn | Leu | Ser | Ser<br>185 | Thr | Val | Ser | Pro<br>190 | Ser | Glu | Glu |
| Tyr | Trp | Ser<br>195 | Arg | Tyr | Val | Leu | His<br>200 | Ile | Gln | Gly | Ser | Gln<br>205 | Gly | Ile | Gly |
| Arg | Pro<br>210 | Gly | Glu | Ile | Arg | Trp<br>215 | Asn | Leu | Cys | Leu | Cys<br>220 | Leu | Leu | Leu | Ala |
| Trp<br>225 | Val | Ile | Val | Phe | Leu<br>230 | Cys | Ile | Leu | Lys | Gly<br>235 | Val | Lys | Ser | Ser | Gly<br>240 |
| Arg | Val | Val | Tyr | Phe<br>245 | Thr | Ala | Thr | Phe | Pro<br>250 | Tyr | Leu | Ile | Leu<br>255 | Leu | Met |
| Leu | Leu | Val | Arg<br>260 | Gly | Val | Thr | Leu | Pro<br>265 | Gly | Ala | Trp | Lys<br>270 | Gly | Ile | Gln |
| Phe | Tyr | Leu<br>275 | Thr | Pro | Gln | Phe | His<br>280 | His | Leu | Leu | Ser | Ser<br>285 | Lys | Val | Trp |
| Ile<br>290 | Glu | Ala | Ala | Leu | Gln<br>295 | Ile | Phe | Tyr | Ser | Leu<br>300 | Gly | Val | Gly | Phe | Gly |
| Gly<br>305 | Leu | Leu | Thr | Phe<br>310 | Ala | Ser | Tyr | Asn | Thr<br>315 | Phe | His | Gln | Asn | Ile | Tyr<br>320 |
| Arg | Asp | Thr | Phe<br>325 | Ile | Val | Thr | Leu | Gly<br>330 | Asn | Ala | Ile | Thr<br>335 | Ser | Ile | Leu |
| Ala | Gly | Phe | Ala<br>340 | Ile | Phe | Ser | Val | Leu<br>345 | Gly | Tyr | Met | Ser<br>350 | Gln | Glu | Leu |
| Gly | Val | Pro<br>355 | Val | Asp | Gln | Val | Ala<br>360 | Lys | Ala | Gly | Pro<br>365 | Gly | Leu | Ala | Phe |
| Val | Ile<br>370 | Tyr | Pro | Gln | Ala | Met<br>375 | Thr | Met | Leu | Pro<br>380 | Leu | Ser | Pro | Phe | Trp |
| Ser<br>385 | Phe | Leu | Phe | Phe | Glu<br>390 | Met | Leu | Leu | Thr | Leu<br>395 | Gly | Leu | Asp | Ser | Gln<br>400 |
| Phe | Ala | Phe | Leu | Glu<br>405 | Thr | Ile | Val | Ile | Ala<br>410 | Val | Thr | Asp | Glu | Phe<br>415 | Pro |
| Tyr | Tyr | Leu | Arg<br>420 | Pro | Lys | Lys | Ala | Val<br>425 | Phe | Ser | Gly | Leu | Ile<br>430 | Cys | Val |
| Ala | Met | Tyr<br>435 | Leu | Met | Gly | Leu | Ile<br>440 | Leu | Thr | Thr | Asp | Gly<br>445 | Gly | Met | Tyr |
| Trp | Leu<br>450 | Val | Leu | Leu | Asp | Asp<br>455 | Tyr | Ser | Ala | Ser | Phe<br>460 | Gly | Leu | Met | Val |
| Val<br>465 | Val | Ile | Thr | Thr | Cys<br>470 | Leu | Ala | Val | Thr | Arg<br>475 | Val | Tyr | Gly | Ile | Gln<br>480 |
| Arg | Phe | Cys | Arg | Asp<br>485 | Ile | His | Met | Met | Leu<br>490 | Gly | Phe | Lys | Pro | Gly<br>495 | Leu |
| Tyr | Phe | Arg | Ala<br>500 | Cys | Trp | Leu | Phe | Leu<br>505 | Ser | Pro | Ala | Thr | Leu<br>510 | Leu | Ala |
| Leu | Leu | Val<br>515 | Tyr | Ser | Ile | Val | Lys<br>520 | Tyr | Gln | Pro | Ser | Glu<br>525 | Tyr | Gly | Ser |
| Tyr | Arg<br>530 | Phe | Pro | Ala | Met | Ala<br>535 | Glu | Leu | Leu | Gly | Ile<br>540 | Leu | Met | Gly | Leu |
| Leu<br>545 | Ser | Cys | Leu | Met | Ile<br>550 | Pro | Ala | Gly | Met | Leu<br>555 | Val | Ala | Val | Leu | Arg<br>560 |
| Glu | Glu | Gly | Ser | Leu<br>565 | Trp | Glu | Arg | Leu | Gln<br>570 | Ala | Ser | Arg | Pro<br>575 | Ala |
| Ile | Asp | Trp | Gly<br>580 | Pro | Ser | Leu | Glu | Glu<br>585 | Asn | Arg | Thr | Gly<br>590 | Met | Tyr | Val |

|           |           |           |           |           |           |           |           |           |           |           |           |           |           |           |
|-----------|-----------|-----------|-----------|-----------|-----------|-----------|-----------|-----------|-----------|-----------|-----------|-----------|-----------|-----------|
| Ala       | Thr       | Leu<br>595| Ala       | Gly       | Ser       | Gln       | Ser<br>600| Pro       | Lys       | Pro       | Leu       | Met<br>605| Val       | His       | Met |
| Arg       | Lys<br>610| Tyr       | Gly       | Gly       | Ile       | Thr<br>615| Ser       | Phe       | Glu       | Asn       | Thr<br>620| Ala       | Ile       | Glu       | Val |
| Asp<br>625| Arg       | Glu       | Ile       | Ala       | Glu<br>630| Glu       | Glu       | Glu       | Ser<br>635|           |           |           |           |           |     |

( 2 ) INFORMATION FOR SEQ ID NO:10:

( i ) SEQUENCE CHARACTERISTICS:
        ( A ) LENGTH: 599 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Rattus
        ( F ) TISSUE TYPE: Brain - GABA transporter ( i x ) FEATURE:
        ( A ) NAME/KEY: Active-site
        ( B ) LOCATION: 83..84
        ( D ) OTHER INFORMATION: /note="Leucine zipper motif"

( i x ) FEATURE:
        ( A ) NAME/KEY: Active-site
        ( B ) LOCATION: 90..91
        ( D ) OTHER INFORMATION: /note="Leucine zipper motif"

( i x ) FEATURE:
        ( A ) NAME/KEY: Active-site
        ( B ) LOCATION: 97..98
        ( D ) OTHER INFORMATION: /note="Leucine zipper motif"

( i x ) FEATURE:
        ( A ) NAME/KEY: Active-site
        ( B ) LOCATION: 104..105
        ( D ) OTHER INFORMATION: /note="Leucine zipper motif"

( x i ) SEQUENCE DESCRIPTION: SEQ ID NO:10:

|           |           |           |           |           |           |           |           |           |           |           |           |           |           |           |
|-----------|-----------|-----------|-----------|-----------|-----------|-----------|-----------|-----------|-----------|-----------|-----------|-----------|-----------|-----------|
| Met<br>1  | Ala       | Thr       | Asp       | Asn<br>5  | Ser       | Lys       | Val       | Ala       | Asp<br>10 | Gly       | Gln       | Ile       | Ser       | Thr<br>15 | Glu |
| Val       | Ser       | Glu       | Ala<br>20 | Pro       | Val       | Ala       | Ser       | Asp<br>25 | Lys       | Pro       | Lys       | Thr       | Leu<br>30 | Val       | Val |
| Lys       | Val       | Gln<br>35 | Lys       | Lys       | Ala       | Gly       | Asp<br>40 | Leu       | Pro       | Asp       | Arg       | Asp<br>45 | Thr       | Trp       | Lys |
| Gly       | Arg<br>50 | Phe       | Asp       | Phe       | Leu       | Met<br>55 | Ser       | Cys       | Val       | Gly       | Tyr<br>60 | Ala       | Ile       | Gly       | Leu |
| Gly<br>65 | Asn       | Val       | Trp       | Arg       | Glu<br>70 | Pro       | Tyr       | Leu       | Cys       | Gly<br>75 | Lys       | Asn       | Gly       | Gly       | Gly<br>80 |
| Ala       | Phe       | Leu       | Ile       | Pro<br>85 | Tyr       | Phe       | Leu       | Thr       | Leu<br>90 | Ile       | Phe       | Ala       | Gly       | Val<br>95 | Pro |
| Leu       | Phe       | Leu       | Leu<br>100| Glu       | Cys       | Ser       | Leu       | Gly<br>105| Gln       | Tyr       | Thr       | Ser       | Ile<br>110| Gly       | Gly |
| Leu       | Gly       | Val<br>115| Met       | Lys       | Leu       | Ala       | Pro<br>120| Met       | Phe       | Lys       | Gly       | Val<br>125| Gly       | Leu       | Ala |
| Ala       | Ala<br>130| Val       | Leu       | Ser       | Phe       | Trp<br>135| Leu       | Asn       | Ile       | Tyr       | Tyr<br>140| Ile       | Val       | Ile       | Ile |

```
Ser  Trp  Ala  Ile  Tyr  Tyr  Leu  Tyr  Asn  Ser  Phe  Thr  Thr  Thr  Leu  Pro
145                      150                     155                     160

Trp  Lys  Gln  Cys  Asp  Asn  Pro  Trp  Asn  Thr  Asp  Arg  Cys  Phe  Ser  Asn
                    165                     170                     175

Tyr  Ser  Leu  Val  Asn  Thr  Thr  Asn  Met  Thr  Ser  Ala  Val  Val  Glu  Phe
               180                     185                     190

Trp  Glu  Arg  Asn  Met  His  Gln  Met  Thr  Asp  Gly  Leu  Asp  Lys  Pro  Gly
          195                     200                     205

Gln  Ile  Arg  Trp  Pro  Leu  Ala  Ile  Thr  Leu  Ala  Ile  Ala  Trp  Val  Leu
     210                     215                     220

Val  Tyr  Phe  Cys  Ile  Trp  Lys  Gly  Val  Gly  Trp  Thr  Gly  Lys  Val  Val
225                      230                     235                     240

Tyr  Phe  Ser  Ala  Thr  Tyr  Pro  Tyr  Ile  Met  Leu  Ile  Ile  Leu  Phe  Phe
               245                     250                     255

Arg  Gly  Val  Thr  Leu  Pro  Gly  Ala  Lys  Glu  Gly  Ile  Leu  Phe  Tyr  Ile
               260                     265                     270

Thr  Pro  Asn  Phe  Arg  Lys  Leu  Ser  Asp  Ser  Glu  Val  Trp  Leu  Asp  Ala
          275                     280                     285

Ala  Thr  Gln  Ile  Phe  Phe  Asx  Tyr  Gly  Leu  Gly  Leu  Gly  Ser  Leu  Ile
290                     295                     300

Ala  Leu  Gly  Ser  Tyr  Asn  Ser  Phe  His  Asn  Asn  Val  Tyr  Arg  Asp  Ser
305                     310                     315                     320

Ile  Ile  Val  Cys  Cys  Ile  Asn  Ser  Cys  Thr  Ser  Met  Phe  Ala  Gly  Phe
               325                     330                     335

Val  Ile  Phe  Ser  Ile  Val  Gly  Phe  Met  Ala  His  Val  Thr  Lys  Arg  Ser
               340                     345                     350

Ile  Ala  Asp  Val  Ala  Ala  Ser  Gly  Pro  Gly  Leu  Ala  Phe  Leu  Ala  Tyr
          355                     360                     365

Pro  Glu  Ala  Val  Thr  Gln  Leu  Pro  Ile  Ser  Pro  Leu  Trp  Ala  Ile  Leu
     370                     375                     380

Phe  Phe  Ser  Met  Leu  Leu  Met  Leu  Gly  Ile  Asp  Ser  Gln  Phe  Cys  Thr
385                     390                     395                     400

Val  Glu  Gly  Phe  Ile  Thr  Ala  Leu  Val  Asp  Glu  Tyr  Pro  Arg  Leu  Leu
               405                     410                     415

Arg  Asn  Arg  Arg  Glu  Leu  Phe  Ile  Ala  Ala  Val  Cys  Ile  Val  Ser  Tyr
               420                     425                     430

Leu  Ile  Gly  Leu  Ser  Asn  Ile  Thr  Gln  Gly  Gly  Ile  Tyr  Val  Phe  Lys
          435                     440                     445

Leu  Phe  Asp  Tyr  Tyr  Ser  Ala  Ser  Gly  Met  Ser  Leu  Leu  Phe  Leu  Val
     450                     455                     460

Phe  Phe  Glu  Cys  Val  Ser  Ile  Ser  Trp  Phe  Tyr  Gly  Val  Asn  Arg  Phe
465                     470                     475                     480

Tyr  Asp  Asn  Ile  Gln  Glu  Met  Val  Gly  Ser  Arg  Pro  Cys  Ile  Trp  Trp
               485                     490                     495

Lys  Leu  Cys  Trp  Ser  Phe  Phe  Thr  Pro  Ile  Ile  Val  Ala  Gly  Val  Phe
               500                     505                     510

Leu  Phe  Ser  Ala  Val  Gln  Met  Thr  Pro  Leu  Thr  Met  Gly  Ser  Tyr  Val
          515                     520                     525

Phe  Pro  Lys  Trp  Gly  Gln  Gly  Val  Gly  Trp  Leu  Met  Ala  Leu  Ser  Ser
     530                     535                     540

Met  Val  Leu  Ile  Pro  Gly  Tyr  Met  Ala  Tyr  Met  Phe  Leu  Thr  Leu  Lys
545                     550                     555                     560

Gly  Ser  Leu  Lys  Gln  Arg  Leu  Gln  Val  Met  Ile  Gln  Pro  Ser  Glu  Asp
               565                     570                     575
```

Ile Val Arg Pro Glu Asn Gly Pro Glu Gln Pro Gln Ala Gly Ser Ser
                580                 585                 590

Ala Ser Lys Glu Ala Tyr Ile
        595

( 2 ) INFORMATION FOR SEQ ID NO:11:

( i ) SEQUENCE CHARACTERISTICS:
        ( A ) LENGTH: 617 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Homo sapiens
        ( F ) TISSUE TYPE: Brain - norepinephrine transporter ( i x ) FEATURE:
        ( A ) NAME/KEY: Active-site
        ( B ) LOCATION: 95..96
        ( D ) OTHER INFORMATION: /note="Leucine zipper motif"

( i x ) FEATURE:
        ( A ) NAME/KEY: Active-site
        ( B ) LOCATION: 102..103
        ( D ) OTHER INFORMATION: /note="Leucine zipper motif"

( i x ) FEATURE:
        ( A ) NAME/KEY: Active-site
        ( B ) LOCATION: 109..110
        ( D ) OTHER INFORMATION: /note="Leucine zipper motif"

( i x ) FEATURE:
        ( A ) NAME/KEY: Active-site
        ( B ) LOCATION: 116..117
        ( D ) OTHER INFORMATION: /note="Leucine zipper motif"

( x i ) SEQUENCE DESCRIPTION: SEQ ID NO:11:

Met Leu Leu Ala Arg Met Asn Pro Gln Val Gln Pro Glu Asn Asn Gly
1               5                   10                  15

Ala Asp Thr Gly Pro Glu Gln Pro Leu Arg Ala Arg Lys Thr Ala Glu
            20                  25                  30

Leu Leu Val Val Lys Glu Arg Asn Gly Val Gln Cys Leu Leu Ala Pro
        35                  40                  45

Arg Asp Gly Asp Ala Gln Pro Arg Glu Thr Trp Gly Lys Lys Ile Asp
    50                  55                  60

Phe Leu Leu Ser Val Val Gly Phe Ala Val Asp Leu Ala Asn Val Trp
65                  70                  75                  80

Arg Phe Pro Tyr Leu Cys Tyr Lys Asn Gly Gly Gly Ala Phe Leu Ile
                85                  90                  95

Pro Tyr Thr Leu Phe Leu Ile Ile Ala Gly Met Pro Leu Phe Tyr Met
                100                 105                 110

Glu Leu Ala Leu Gly Gln Tyr Asn Arg Glu Gly Ala Ala Thr Val Trp
            115                 120                 125

Lys Ile Cys Pro Phe Phe Lys Gly Val Gly Tyr Ala Val Ile Leu Ile
    130                 135                 140

Ala Leu Tyr Val Gly Phe Tyr Tyr Asn Val Ile Ile Ala Trp Ser Leu
145                 150                 155                 160

```
Tyr  Tyr  Leu  Phe  Ser  Ser  Phe  Thr  Leu  Asn  Leu  Pro  Trp  Thr  Asp  Cys
               165            170                           175

Gly  His  Thr  Trp  Asn  Ser  Pro  Asn  Cys  Thr  Asp  Pro  Lys  Leu  Leu  Asn
               180            185                           190

Gly  Ser  Val  Leu  Gly  Asn  His  Thr  Lys  Tyr  Ser  Lys  Tyr  Lys  Phe  Thr
               195            200                           205

Pro  Ala  Ala  Glu  Phe  Tyr  Glu  Arg  Gly  Val  Leu  His  Leu  His  Glu  Ser
     210            215                           220

Ser  Gly  Ile  His  Asp  Ile  Gly  Leu  Pro  Gln  Trp  Gln  Leu  Leu  Leu  Cys
225                 230                 235                                240

Leu  Met  Val  Val  Val  Ile  Val  Leu  Tyr  Phe  Ser  Leu  Trp  Lys  Gly  Val
                    245                 250                           255

Lys  Thr  Ser  Gly  Lys  Val  Val  Trp  Ile  Thr  Ala  Thr  Leu  Pro  Tyr  Phe
               260                 265                           270

Val  Leu  Phe  Val  Leu  Leu  Val  His  Gly  Val  Thr  Leu  Pro  Gly  Ala  Ser
               275                 280                           285

Asn  Gly  Ile  Asn  Ala  Tyr  Leu  His  Ile  Asp  Phe  Tyr  Arg  Leu  Lys  Glu
     290                      295                      300

Ala  Thr  Val  Trp  Ile  Asp  Ala  Ala  Thr  Gln  Ile  Phe  Phe  Ser  Leu  Gly
305                      310                 315                           320

Ala  Gly  Phe  Gly  Val  Leu  Ile  Ala  Phe  Ala  Ser  Tyr  Asn  Lys  Phe  Asp
               325                      330                           335

Asn  Asn  Cys  Tyr  Arg  Asp  Ala  Leu  Leu  Thr  Ser  Ser  Ile  Asn  Cys  Ile
               340                      345                      350

Thr  Ser  Phe  Val  Ser  Gly  Phe  Ala  Ile  Phe  Ser  Ile  Leu  Gly  Tyr  Met
          355                      360                 365

Ala  His  Glu  His  Lys  Val  Asn  Ile  Glu  Asp  Val  Ala  Thr  Glu  Gly  Ala
     370                      375                 380

Gly  Leu  Val  Phe  Ile  Leu  Tyr  Pro  Glu  Ala  Ile  Ser  Thr  Leu  Ser  Gly
385                      390                 395                           400

Ser  Thr  Phe  Trp  Ala  Val  Val  Phe  Phe  Val  Met  Leu  Leu  Ala  Leu  Gly
                    405                 410                           415

Leu  Asp  Ser  Ser  Met  Gly  Gly  Met  Glu  Ala  Val  Ile  Thr  Gly  Leu  Ala
               420                 425                           430

Asp  Asp  Phe  Gln  Val  Leu  Lys  Arg  His  Arg  Lys  Leu  Phe  Thr  Phe  Gly
          435                 440                      445

Val  Thr  Phe  Ser  Thr  Phe  Leu  Leu  Ala  Leu  Phe  Cys  Ile  Thr  Lys  Gly
     450                 455                      460

Gly  Ile  Tyr  Val  Leu  Thr  Leu  Leu  Asp  Thr  Phe  Ala  Ala  Gly  Thr  Ser
465                      470                 475                           480

Ile  Leu  Phe  Ala  Val  Leu  Met  Glu  Ala  Ile  Gly  Val  Ser  Trp  Phe  Tyr
               485                 490                           495

Gly  Val  Asp  Arg  Phe  Ser  Asn  Asp  Ile  Gln  Gln  Met  Met  Gly  Phe  Arg
               500                 505                      510

Pro  Gly  Leu  Tyr  Trp  Arg  Leu  Cys  Trp  Lys  Phe  Val  Ser  Pro  Ala  Phe
          515                 520                      525

Leu  Leu  Phe  Val  Val  Val  Val  Ser  Ile  Ile  Asn  Phe  Lys  Pro  Leu  Thr
     530                 535                      540

Tyr  Asp  Asp  Tyr  Ile  Phe  Pro  Pro  Trp  Ala  Asn  Trp  Val  Gly  Trp  Gly
545                      550                 555                           560

Ile  Ala  Leu  Ser  Ser  Met  Val  Leu  Val  Pro  Ile  Tyr  Val  Ile  Tyr  Lys
               565                 570                           575

Phe  Leu  Ser  Thr  Gln  Gly  Ser  Leu  Trp  Glu  Arg  Leu  Ala  Tyr  Gly  Ile
          580                 585                           590
```

Thr Pro Glu Asn Glu His His Leu Val Ala Gln Arg Asp Ile Arg Gln
    595                 600                 605

Phe Gln Leu Gln His Trp Leu Ala Ile
    610                 615

( 2 ) INFORMATION FOR SEQ ID NO:12:

( i ) SEQUENCE CHARACTERISTICS:
        ( A ) LENGTH: 607 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: NO ( i v ) ANTI-SENSE: NO ( v ) FRAGMENT TYPE: N-terminal ( v i ) ORIGINAL SOURCE:
        ( A ) ORGANISM: Rattus
        ( F ) TISSUE TYPE: Brain - serotonin transporter ( i x ) FEATURE:
        ( A ) NAME/KEY: Active-site
        ( B ) LOCATION: 95..96
        ( D ) OTHER INFORMATION: /note="Leucine zipper motif"

( i x ) FEATURE:
        ( A ) NAME/KEY: Active-site
        ( B ) LOCATION: 102..103
        ( D ) OTHER INFORMATION: /note="Leucine zipper motif"

( i x ) FEATURE:
        ( A ) NAME/KEY: Active-site
        ( B ) LOCATION: 109..110
        ( D ) OTHER INFORMATION: /note="Leucine zipper motif"

( i x ) FEATURE:
        ( A ) NAME/KEY: Active-site
        ( B ) LOCATION: 116..117
        ( D ) OTHER INFORMATION: /note="Leucine zipper motif"

( x i ) SEQUENCE DESCRIPTION: SEQ ID NO:12:

Met Val Phe Tyr Arg Arg Val Ser Pro Pro Gln Arg Thr Gly Gln Ser
1                5                  10                  15

Leu Ala Lys Tyr Pro Met Gly Thr Leu Gln Ser Pro Gly Thr Ser Ala
            20                  25                  30

Gly Asp Glu Ala Ser His Ser Ile Pro Ala Ala Thr Thr Thr Leu Val
            35                  40                  45

Ala Glu Ile Arg Gln Gly Glu Arg Glu Thr Trp Gly Lys Lys Met Asp
    50                  55                  60

Phe Leu Leu Ser Val Ile Gly Tyr Ala Val Asp Leu Gly Asn Ile Trp
65                  70                  75                  80

Arg Phe Pro Tyr Ile Cys Tyr Gln Asn Gly Gly Gly Ala Phe Leu Leu
                85                  90                  95

Pro Tyr Thr Ile Met Ala Ile Phe Gly Gly Ile Pro Leu Phe Tyr Met
            100                 105                 110

Glu Leu Ala Leu Gly Gln Tyr His Arg Asn Gly Cys Ile Ser Ile Trp
            115                 120                 125

Arg Lys Ile Cys Pro Ile Phe Lys Gly Ile Gly Tyr Ala Ile Cys Ile
    130                 135                 140

Ile Ala Phe Tyr Ile Ala Ser Tyr Tyr Asn Thr Ile Ile Ala Trp Ala
145                 150                 155                 160

| | | | | | | | | | | | | | | |
|---|---|---|---|---|---|---|---|---|---|---|---|---|---|---|
| Leu | Tyr | Tyr | Leu | Ile 165 | Ser | Ser | Leu | Thr 170 | Asp | Arg | Leu | Pro | Trp 175 | Ser |
| Cys | Thr | Asn 180 | Ser | Trp | Asn | Thr | Gly 185 | Asn | Cys | Thr | Asn | Tyr 190 | Phe | Ala | Gln |
| Asp | Asn | Ile 195 | Thr | Trp | Thr | Leu | His 200 | Ser | Thr | Ser | Pro | Ala 205 | Glu | Glu | Phe |
| Tyr | Leu 210 | Arg | His | Val | Leu | Gln 215 | Ile | His | Gln | Ser | Lys 220 | Gly | Leu | Gln | Asp |
| Leu 225 | Gly | Thr | Ile | Ser | Trp 230 | Gln | Leu | Thr | Leu | Cys 235 | Ile | Val | Leu | Ile | Phe 240 |
| Thr | Val | Ile | Tyr | Phe 245 | Ser | Ile | Trp | Lys | Gly 250 | Val | Lys | Thr | Ser | Gly 255 | Lys |
| Val | Val | Trp | Val 260 | Thr | Ala | Thr | Phe | Pro 265 | Tyr | Ile | Val | Leu | Ser 270 | Val | Leu |
| Leu | Val | Arg 275 | Gly | Ala | Thr | Leu | Phe 280 | Gly | Ala | Trp | Arg | Gly 285 | Val | Val | Phe |
| Tyr | Leu 290 | Lys | Pro | Asn | Trp | Gln 295 | Lys | Leu | Leu | Glu | Thr 300 | Gly | Val | Trp | Val |
| Asp 305 | Ala | Ala | Ala | Gln | Ile 310 | Phe | Phe | Ser | Leu | Gly 315 | Pro | Gly | Phe | Gly | Val 320 |
| Leu | Leu | Ala | Phe | Ala 325 | Ser | Tyr | Asn | Lys | Phe 330 | Asn | Asn | Asn | Cys | Tyr 335 | Gln |
| Asp | Ala | Leu | Val 340 | Thr | Ser | Val | Val | Asn 345 | Cys | Met | Thr | Ser | Phe 350 | Val | Ser |
| Gly | Phe | Val 355 | Ile | Phe | Thr | Val | Leu 360 | Gly | Tyr | Met | Ala | Glu 365 | Met | Arg | Asn |
| Glu | Asp 370 | Val | Ser | Glu | Val | Ala 375 | Lys | Asp | Ala | Gly | Pro 380 | Ser | Leu | Leu | Phe |
| Ile 385 | Thr | Tyr | Ala | Glu | Ala 390 | Ile | Ala | Asn | Met | Pro 395 | Ala | Ser | Thr | Phe | Phe 400 |
| Ala | Ile | Ile | Phe | Phe 405 | Leu | Met | Leu | Ile | Thr 410 | Leu | Gly | Leu | Asp | Ser 415 | Thr |
| Phe | Ala | Gly | Leu 420 | Glu | Gly | Val | Ile | Thr 425 | Ala | Val | Leu | Asp | Glu 430 | Phe | Pro |
| His | Ile | Trp 435 | Ala | Lys | Arg | Arg | Glu 440 | Trp | Phe | Val | Leu | Ile 445 | Val | Val | Ile |
| Thr | Cys 450 | Val | Leu | Gly | Ser | Leu 455 | Leu | Thr | Leu | Thr | Ser 460 | Gly | Gly | Ala | Tyr |
| Val 465 | Val | Thr | Leu | Leu | Glu 470 | Glu | Tyr | Ala | Thr | Gly 475 | Pro | Ala | Val | Leu | Thr 480 |
| Val | Ala | Leu | Ile | Glu 485 | Ala | Val | Ala | Val | Ser 490 | Trp | Phe | Tyr | Gly | Ile 495 | Thr |
| Gln | Phe | Cys | Ser 500 | Asp | Val | Lys | Glu | Met 505 | Leu | Gly | Phe | Ser | Pro 510 | Gly | Trp |
| Phe | Trp | Arg 515 | Ile | Cys | Trp | Val | Ala 520 | Ile | Ser | Pro | Leu | Phe 525 | Leu | Leu | Phe |
| Ile | Ile 530 | Cys | Ser | Phe | Leu | Met 535 | Ser | Pro | Pro | Gln | Leu 540 | Arg | Leu | Phe | Gln |
| Tyr 545 | Asn | Tyr | Pro | His | Trp 550 | Ser | Ile | Val | Leu | Gly 555 | Tyr | Cys | Ile | Gly | Met 560 |
| Ser | Ser | Val | Ile | Cys 565 | Ile | Pro | Thr | Tyr | Ile 570 | Ile | Tyr | Arg | Leu | Ile 575 | Ser |
| Thr | Pro | Gly | Thr 580 | Leu | Lys | Glu | Arg | Ile 585 | Ile | Lys | Ser | Ile | Thr 590 | Pro | Glu |

```
              Thr  Pro  Thr  Glu  Ile  Pro  Cys  Gly  Asp  Ile  Arg  Met  Asn  Ala  Val
                        595                 600                      605
```

(2) INFORMATION FOR SEQ ID NO:13:

(i) SEQUENCE CHARACTERISTICS:
        (A) LENGTH: 616 amino acids
        (B) TYPE: amino acid
        (C) STRANDEDNESS: single
        (D) TOPOLOGY: linear (ii) MOLECULE TYPE: protein (iii) HYPOTHETICAL: NO (iv) ANTI-SENSE: NO (v) FRAGMENT TYPE: N-terminal (vi) ORIGINAL SOURCE:
        (A) ORGANISM: Rattus
        (F) TISSUE TYPE: Brain - dopamine transporter (ix) FEATURE:
        (A) NAME/KEY: Active-site
        (B) LOCATION: 99..100
        (D) OTHER INFORMATION: /note="Leucine zipper motif"

(ix) FEATURE:
        (A) NAME/KEY: Active-site
        (B) LOCATION: 106..107
        (D) OTHER INFORMATION: /note="Leucine zipper motif"

(ix) FEATURE:
        (A) NAME/KEY: Active-site
        (B) LOCATION: 113..114
        (D) OTHER INFORMATION: /note="Leucine zipper motif"

(ix) FEATURE:
        (A) NAME/KEY: Active-site
        (B) LOCATION: 120..121
        (D) OTHER INFORMATION: /note="Leucine zipper motif"

(xi) SEQUENCE DESCRIPTION: SEQ ID NO:13:

```
Met  Ser  Lys  Ser  Lys  Cys  Ser  Val  Gly  Pro  Met  Ser  Ser  Val  Val  Ala
  1              5                        10                       15

Pro  Ala  Lys  Glu  Ser  Asn  Ala  Val  Gly  Pro  Arg  Glu  Val  Glu  Leu  Ile
               20                        25                       30

Leu  Val  Lys  Glu  Gln  Asn  Gly  Val  Gln  Leu  Thr  Asn  Ser  Thr  Leu  Ile
               35                        40                       45

Asn  Pro  Pro  Gln  Thr  Pro  Val  Glu  Ala  Gln  Glu  Arg  Glu  Thr  Trp  Ser
     50                        55                       60

Lys  Lys  Ile  Asp  Phe  Leu  Leu  Ser  Val  Ile  Gly  Phe  Ala  Val  Asp  Leu
 65                      70                       75                       80

Ala  Asn  Val  Trp  Arg  Phe  Pro  Tyr  Leu  Cys  Tyr  Lys  Asn  Gly  Gly  Gly
                    85                       90                       95

Ala  Phe  Leu  Val  Pro  Tyr  Leu  Leu  Phe  Met  Val  Ile  Ala  Gly  Met  Pro
               100                      105                      110

Leu  Phe  Tyr  Met  Glu  Leu  Ala  Leu  Gly  Gln  Phe  Asn  Arg  Glu  Gly  Ala
               115                      120                      125

Ala  Gly  Val  Trp  Lys  Ile  Cys  Pro  Val  Leu  Lys  Gly  Val  Gly  Phe  Thr
     130                      135                      140

Val  Ile  Leu  Ile  Ser  Phe  Tyr  Val  Gly  Phe  Phe  Asn  Val  Ile  Ile  Ala
145                           150                      155                 160

Trp  Ala  Leu  His  Tyr  Phe  Phe  Ser  Ser  Phe  Thr  Met  Asp  Leu  Pro  Trp
               165                      170                      175
```

| | | | | | | | | | | | | | | |
|---|---|---|---|---|---|---|---|---|---|---|---|---|---|---|
| Ile | His | Cys | Asn<br>180 | Asn | Thr | Trp | Asn | Ser<br>185 | Pro | Asn | Cys | Ser | Asp<br>190 | Ala | His |
| Ala | Ser | Asn<br>195 | Ser | Ser | Asp | Gly<br>200 | Leu | Gly | Leu | Asn | Asp<br>205 | Thr | Phe | Gly | Thr |
| Thr | Pro<br>210 | Ala | Ala | Glu | Tyr | Phe<br>215 | Glu | Arg | Gly | Val | Leu<br>220 | His | Leu | His | Gln |
| Ser<br>225 | Arg | Gly | Ile | Asp | Asp<br>230 | Leu | Gly | Pro | Pro | Arg<br>235 | Trp | Gln | Leu | Thr | Ala<br>240 |
| Leu | Val | Leu | Val | Ile<br>245 | Val | Leu | Leu | Tyr | Phe<br>250 | Ser | Leu | Trp | Lys | Gly<br>255 | Val |
| Lys | Thr | Ser | Gly<br>260 | Lys | Val | Val | Trp | Ile<br>265 | Thr | Ala | Ile | Met | Tyr<br>270 | Val | Val |
| Leu | Thr | Ala<br>275 | Leu | Leu | Leu | Arg | Gly<br>280 | Val | Ile | Leu | Pro | Gly<br>285 | Ala | Met | Asp |
| Gly | Ile<br>290 | Arg | Ala | Tyr | Leu | Ser<br>295 | Val | Asp | Phe | Tyr | Arg<br>300 | Leu | Cys | Glu | Ala |
| Ser<br>305 | Val | Asn | Ile | Asp | Ala<br>310 | Ala | Thr | Gln | Val | Cys<br>315 | Phe | Ser | Leu | Gly | Val<br>320 |
| Gly | Phe | Gly | Val | Leu<br>325 | Ile | Ala | Phe | Ser | Ser<br>330 | Tyr | Asn | Lys | Phe | Thr<br>335 | Asn |
| Asn | Cys | Tyr | Arg<br>340 | Asp | Ala | Ile | Ile<br>345 | Thr | Thr | Ser | Ile | Asn<br>350 | Ser | Leu | Thr |
| Ser | Phe | Ser<br>355 | Ser | Gly | Phe | Val | Val<br>360 | Phe | Ser | Phe | Leu | Gly<br>365 | Tyr | Met | Ala |
| Gln | Lys | His<br>370 | Asn | Val | Pro | Ile<br>375 | Arg | Asp | Val | Ala | Thr<br>380 | Asp | Gly | Pro | Gly |
| Leu<br>385 | Ile | Phe | Ile | Ile | Tyr<br>390 | Pro | Glu | Ala | Ile | Ala<br>395 | Thr | Leu | Pro | Leu | Ser<br>400 |
| Ser | Ala | Trp | Ala | Ala<br>405 | Val | Phe | Phe | Leu | Met<br>410 | Leu | Leu | Thr | Leu | Gly<br>415 | Leu |
| Asp | Ser | Ala | Met<br>420 | Gly | Gly | Met | Glu | Ser<br>425 | Val | Leu | Thr | Gly | Leu<br>430 | Val | Asp |
| Glu | Phe | Gln<br>435 | Leu | Leu | His | Arg | His<br>440 | Arg | Glu | Leu | Phe | Thr<br>445 | Leu | Gly | Ile |
| Val | Leu<br>450 | Ala | Thr | Phe | Leu | Leu<br>455 | Ser | Leu | Phe | Cys | Val<br>460 | Thr | Asn | Gly | Gly |
| Ile<br>465 | Tyr | Val | Phe | Thr | Leu<br>470 | Leu | Asp | His | Phe | Ala<br>475 | Ala | Gly | Thr | Ser | Leu<br>480 |
| Leu | Phe | Gly | Val | Leu<br>485 | Ile | Glu | Ala | Ile | Gly<br>490 | Val | Ala | Trp | Phe | Tyr<br>495 | Gly |
| Val | Gln | Gln | Phe<br>500 | Ser | Asp | Asp | Ile | Lys<br>505 | Gln | Met | Thr | Gly | Gln<br>510 | Arg | Pro |
| Asn | Leu | Tyr<br>515 | Trp | Arg | Leu | Cys | Trp<br>520 | Lys | Leu | Val | Ser | Pro<br>525 | Cys | Phe | Leu |
| Leu | Tyr<br>530 | Val | Val | Val | Val | Ser<br>535 | Ile | Val | Thr | Phe | Arg<br>540 | Pro | Pro | His | Tyr |
| Gly<br>545 | Ala | Tyr | Ile | Phe | Pro<br>550 | Asp | Trp | Ala | Asn | Ala<br>555 | Leu | Gly | Trp | Ile | Ile<br>560 |
| Ala | Thr | Ser | Ser | Met<br>565 | Ala | Met | Val | Pro | Ile<br>570 | Tyr | Ala | Thr | Tyr | Lys<br>575 | Phe |
| Cys | Ser | Leu | Pro<br>580 | Gly | Ser | Phe | Arg | Glu<br>585 | Lys | Leu | Ala | Tyr | Ala<br>590 | Ile | Thr |
| Pro | Glu | Lys<br>595 | Asp | His | Gln | Leu | Val<br>600 | Asp | Arg | Gly | Glu | Val<br>605 | Arg | Gln | Phe |

| | | | | | | | |
|---|---|---|---|---|---|---|---|
| Thr | Leu | Arg | His | Trp | Leu | Leu | Leu |
| | | 610 | | | | 615 | |